United States Patent
Colman et al.

(10) Patent No.: US 10,178,962 B2
(45) Date of Patent: *Jan. 15, 2019

(54) METHOD AND APPARATUS FOR PRODUCING A WAVEFORM

(71) Applicant: ORIDION MEDICAL 1987 LTD., Jerusalem (IL)

(72) Inventors: Joshua Lewis Colman, Jerusalem (IL); Michal Ronen, Givat-Brenner (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/695,906

(22) Filed: Sep. 5, 2017

(65) Prior Publication Data

US 2018/0116554 A1 May 3, 2018

Related U.S. Application Data

(63) Continuation of application No. 13/379,548, filed as application No. PCT/IL2009/000630 on Jun. 24, 2009, now Pat. No. 9,770,191.

(51) Int. Cl.
*G06T 11/20* (2006.01)
*G09G 5/00* (2006.01)
*A61B 5/08* (2006.01)
*A61B 5/083* (2006.01)

(52) U.S. Cl.
CPC ............. *A61B 5/0836* (2013.01); *A61B 5/08* (2013.01); *G06T 11/20* (2013.01); *G09G 5/00* (2013.01)

(58) Field of Classification Search
None
See application file for complete search history.

(56) References Cited

U.S. PATENT DOCUMENTS

| | | | |
|---|---|---|---|
| 4,245,648 A | 1/1981 | Trimmer et al. | |
| 5,751,911 A | 5/1998 | Goldman et al. | |
| 5,830,149 A * | 11/1998 | Oka | A61B 5/02116 600/500 |
| 7,425,201 B2 | 9/2008 | Euliano et al. | |
| 2002/0082511 A1 * | 6/2002 | Carlebach | A61B 5/0836 600/529 |
| 2006/0129401 A1 | 6/2006 | Smith et al. | |

(Continued)

FOREIGN PATENT DOCUMENTS

| | | |
|---|---|---|
| JP | 2002156388 A | 5/2002 |
| WO | 0074631 | 12/2000 |

(Continued)

*Primary Examiner* — Barry Drennan
*Assistant Examiner* — Schiller Hill
(74) *Attorney, Agent, or Firm* — Fletcher Yoder PC

(57) ABSTRACT

There is provided herein a method for producing a representative CO2 waveform, the method comprising obtaining two or more CO2 waveforms, for each of the two or more CO2 waveforms determining one or more scale factors and one or more shape factors, computing, based on the one or more shape and scale factors of each of the two or more CO2 waveforms, a representative set of shape factors and scale factors representing the two or more CO2 waveforms and constructing a representative waveform based on the representative set of shape and scale factors.

20 Claims, 18 Drawing Sheets

(56) References Cited

U.S. PATENT DOCUMENTS

| | | | |
|---|---|---|---|
| 2008/0009762 A1* | 1/2008 | Hampton | A61B 5/0836 600/532 |
| 2008/0081961 A1* | 4/2008 | Westbrook | A61B 5/0205 600/301 |
| 2008/0082017 A1 | 4/2008 | Savic | |
| 2008/0177195 A1 | 7/2008 | Armitstead | |

FOREIGN PATENT DOCUMENTS

| | | |
|---|---|---|
| WO | 03053503 A1 | 7/2003 |
| WO | 2006012205 A2 | 2/2006 |
| WO | 2006066337 A1 | 6/2006 |

* cited by examiner

METHOD AND APPARATUS FOR PRODUCING A WAVEFORM

CROSS REFERENCE TO RELATED APPLICATION

This application is a continuation of U.S. application Ser. No. 13/379,548, filed on Dec. 20, 2011, now U.S. Pat. No. 9,770,191, the entire contents of which are herein expressly incorporated by reference for all purposes.

FIELD OF THE INVENTION

The invention generally relates to method and apparatus for producing and displaying a waveform, such as a carbon dioxide ($CO_2$) waveform.

BACKGROUND

A waveform generally refers to a shape of a signal, such as a wave, that is moving in a medium (for example, a solid, liquid or gaseous medium). In cases wherein a direct visual image of a shape of a propagated signal cannot be obtained, a waveform, which in these cases may also be referred to as a moving waveform, describes a shape of a graph which is varying over time or distance. In other words a moving waveform shows a series of propagating waves, each representing a different time or distance.

In capnography for example, a capnograph collects samples of a patient's breath, senses and calculates the real time $CO_2$ concentration (as partial $CO_2$ pressure) of the sample. The calculated $CO_2$ concentration over time is depicted on an appropriate display as a moving waveform. The resolution of the moving waveform and the sweep time are such that a user can identify breath cycles on the display. The information obtained in capnography may be used to determine a condition of a patient.

In the case of capnography, the "x" axis of the displayed moving waveform is time and is generally defined for enough time so that at least 2 to 3 wave cycles can be captured. Since different age groups have different breath cycle times, the length of the "x" axis may often be changed as a function of the age. For example, since neonates breathe at relatively fast rates, normally 50 to 80 Breaths per Minute (BPM), the time required to capture at least 2 to 3 wave cycles will be shorter than the time required to capture the same number of wave cycles in adults.

The "y" axis of the displayed moving waveform is defined either in units of partial pressure (mmHg, kpa or other units) or in volume percent (Vol. %). The height of the "y" axis is generally defined such that a standard breath concentration (37 mmHg) will reach close to approximately ⅔ of the axis (for example 50 mmHg). When high $CO_2$ concentrations are realized, this may be increased (for example to 100 mmHg).

In order for a waveform to be at least minimally representative of the changes in $CO_2$ concentration over time in a breath cycle, a reading (or a point) should be taken at least once in every 200 millisecond (msec) for standard adult breath rates, though every 50 msec may be preferred. With high respiration rates up to 150 BPM, it may be imperative to read every 50 msec. The more data points (resolution), the more a user or an operator (such as a physician or a nurse) can observe characteristic shapes in the waveform.

The waveform generally includes both clinically relevant characteristics but also clinically insignificant characteristics on the waveform. In general, clinically irrelevant (insignificant) effects on the waveform originate from external stimuli such as talking, movement, coughing, eating or the like, whereas a clinically significant effect on the waveform may originate from the patient physiological condition, for example, respiratory and/or cardiac condition. Such conditions may include asthma, congestive heart failure (CHF), chronic obstructive pulmonary disease (COPD), sedation or treatment with drugs, such as in pain management or any other medical condition.

In addition to the potential clinical value and relevancy related to the characteristics of each individual waveform, the patterns and characteristics of consecutive waveforms or groups of waveforms and their changes, rates of change and other characteristics may also be relevant. An example of characteristics of consecutive waveforms may be seen in Cheyne Stokes breathing which can be diagnosed only while analyzing consecutive waveforms as opposed to one or two individual waveforms.

There may also be relevancy to a periodicity and repeatability of the waveforms on one hand, and to an erratic behavior and dispersion of the characteristics on the other hand. Sometimes, the clinical meaning of the above may be different for an awaken patient and a patient who is asleep (sedated or unconscious). With intubated patients, the waveforms are generally more repeatable, especially for duration and duty cycle of the breath cycle because of the ventilator settings and generally sedated state of the patient. With non-intubated patients the shapes of each waveform are more sporadic.

Several problems are associated with the displaying and usability of prior art moving waveforms, such as the $CO_2$ concentration moving waveforms produced and presented in capnography. These problems include for example the following:

1. The existing Capnographs show a series of two or three waveforms at a time and they are continuously being built up and crossing the screen relative to the patient's breath cycle, with no synchronization to the axis. In other words, the waveform may sometimes start in the middle of a breath cycle at "x" (time)=0, or may start towards the end of breath cycle, depending on how the respiration rate (RR) fits the time span given for the "x" axis displayed. This moving waveform makes it difficult to focus on characteristics and changes of the waveform which may be of interest.

2. A user (such as a physician or a nurse) can only compare between two or three waves at any given time, hence patterns over groups and sets of waveforms are difficult and sometimes impossible to notice.

3. There are many artifacts that can cause changes to each waveform which makes it difficult to distinguish between patterns that have physiological/clinical importance and patterns which are only artifacts.

4. In addition to the many possible shapes of the waveform, there are also the scale factors of the waveform. The scale factors include heights, widths, duty cycles and the like. In spontaneous breathing patients particularly, these scale factors become an infinite number of possible combinations, changing on the screen at all the time, many of them are not yet understood even by respiratory experts.

5. Characteristics of the waveform that may have physiological/clinical significance are often slight and not easily recognized, for example, for some of the reasons mentioned above (even if the user is well versed in these patterns). 6. It is difficult to differentiate between dominant, recurring patterns and those that are erratic, non-recurring patterns.

7. Although, in addition to real time sweeping of the moving waveform, a capnograph for example, may also provide trend data (for example, of the End-Tidal Carbon Dioxide, EtCO$_2$) of the waveforms, and sometimes an ability to return to a waveform from the past related to an event or requested reference, this requires large memory banks which would require a very strong computer with large memory to save even a few hours of previous waveforms.

8. It is difficult to notice a change in certain characteristics of a waveform (for example, slopes or other characteristics) without the ability to compare with a reference and/or a baseline.

These problems and others often create a feeling of desperation by nurses and doctors regarding the usability of these waveforms besides receiving a visual sign that there is a breathing cycle occurring.

There is thus a need in the art for methods and apparatuses that would produce usable waveforms.

SUMMARY

This summary section of the patent application is intended to provide an overview of the subject matter disclosed herein, in a form lengthier than an "abstract", and should not be construed as limiting the invention to any features described in this summary section.

Some embodiments of the invention are generally directed to a method and apparatus for producing (or in other words, reconstructing) and optionally displaying a representative waveform, for example, a waveform of the changes in CO$_2$ concentration over time. According to some embodiments, producing a representative waveform may include producing a waveform that is representative of "x" seconds of waveform obtaining (for example, the last "x" seconds), or "y" waveforms (for example, the last "y" waveforms). The resulting representative waveform may include the medically significant information obtained from the one or more "y" waveforms or form the one or more waveforms captured during the "x" seconds, while non-reoccurring events having no known significance, artifacts and/or other factors which are not medically relevant or not desired are removed entirely or suppressed. The production of one representative waveform, which shows relevant medical information while eliminating the non-significant information, increases the degree of usability of such waveforms. For example, displaying the representative waveform may help a user obtain less data (one representative waveform instead of constantly progressing chain of single waveforms) without loosing valuable medical information.

According to some embodiments, the term "representative waveform" may refer to any waveform that can represent a set of waveforms. The set of waveforms may include a predetermined number of waveforms or any number of waveforms obtained over a predetermined period of time.

According to some embodiments, a waveform can be characterized by two types of factors, namely shape factors and by scale factors.

Shape factors characterize and/or describe the shape or pattern of the waveform. A shape factor may include, for example, parameters of a non-linear function describing an upstroke of the waveform. The shape factors of the waveform are generally indicative of physiological condition(s) of a patient. For example, dominant shape factors of the waveform(s) may relate to respiratory process such as the mechanics of breathing. Shape factors may be parameters of a function or set of binary values (in the form of a vector or a matrix).

Scale factors are the waveform values and/or ratios, for example, height, width, width at half-height, duty cycle, I to E (Inhalation to Exhalation) ratio or any other value or combination of values. Scale factor features typically relate to general processes and/or body functions, such as, perfusion, shunt, metabolism, ventilation, respiration and the like. For example (which is presented herein merely for better showing the difference between shape factor and scale factor), a waveform may show a "perfect" textbook (normal) shape, normal shape factors, but the height of the waveform (which is considered as a "scale factor") is very low. This may be a result of, for example, normal lung mechanics but low perfusion resulting from trauma.

According to some embodiments, a representative waveform can be characterized by a representative set of shape factors and scale factors describing the waveforms which are represented by the representative waveform (for example, the waveforms obtained over "x" seconds or "y" waveforms).

According to some embodiments of the invention, the method of producing the representative waveform may include determining one or more shape factors of one or more waveforms (as realized over "x" seconds or "y" waveforms). The method may further include analyzing the one or more shape factors of one or more waveforms.

According to some embodiments of the invention, the method of producing the representative waveform may include determining one or more scale factors of one or more waveforms (as realized over "x" seconds or "y" waveforms). The method may further include analyzing one or more scale factors of one or more waveforms. The analysis of the one or more scale factors of one or more waveforms may include for example, using their basic average values.

According to some embodiments of the invention, the representative waveform may be constructed by analyzing essentially separately the one or more shape factors and the one or more scale factors. While the scale factors may be analyzed using their basic average values, the shape factors may require a more complicated mathematical analysis (such as fit to linear or non-linear function, classification or the like). When the shape factors and scale factors are being analyzed separately as two independent types of features of the waveform, the result may be integrated together to form one representative waveform. According to some embodiments of the invention, the representative waveform may be cleaned from artifacts, while still include reoccurring and/or dominant characteristics. In other words, the method for producing the representative waveform may include eliminating or suppressing artifacts while presenting reoccurring and/or dominant shape factors.

According to some embodiments of the invention, the representative waveform may be displayed starting from a given point in the breath cycle so that it is not moving along the screen and starting at different positions. The representative waveform may be updated at different given predefined rates, for example, once in every 10-20 seconds or at any other rate. The update rate may be defined by a user or may be a function of specific parameter(s) and/or condition(s), for example, respiration rate (RR), age of the patient, a disease of the patient or any other parameter(s) and/or condition(s). The update rate may be dynamically changed during the monitoring period.

According to some embodiments of the invention, the representative waveform may be displayed over a background waveform. For example, the representative waveform may be displayed over a baseline waveform. The baseline waveform may include a waveform (or a set of waveforms) taken prior to a beginning of a medical treatment, such as sedation, drug therapy, pain management, surgical procedure or the like. The baseline waveform may also include a representative waveform of waveforms taken at a certain time or condition (such as sedation, drug therapy, pain management, surgical procedure or the like). This presentation may allow a user to have some understanding related to the trend of the waveform or the change thereof which may be a result of such treatment.

The representative waveform may also be displayed over a background of a "normal" waveform. The "normal" waveform may include an averaged waveform of healthy population of subjects and may also be more specifically selected based on the particular patient being monitored, for example, based on the age, gender, medical history, medical condition or the like.

The representative waveform may also be displayed over "normal" waveform regions. This presentation may allow a user to see whether the representative waveform (which, as mentioned above, may be updated at a certain rate) is still within a normal range. Upon request the representative waveform can also be displayed upon a second displayed background region that defines the minimum and maximum waveforms that were used to build this representative waveform. The background region may also indicate the standard deviation or other values indicating variability or spread of the waveforms that were used to build this representative waveform.

The representative waveform may also be displayed upon one or more preceding representative waveforms in order to show the progress and/or changes over time. The preceding waveforms may be displayed in such way so that it is clear to a user that they relate to the past as opposed to the current representative waveform.

According to some embodiments of the invention, for comparison analysis, the representative waveform may be compared with a baseline waveform (such as a representative baseline waveform), with any waveform or representative waveform from the past or with a library of predefined waveforms that may be indicative of specific clinical condition(s) (such as asthma, for example). The waveform used for comparison may be automatically chosen or manually chosen by the user. Similarity programs may also be used to show the relevancy or the medical significance resulting from the comparison.

Producing (or reconstructing) a representative waveform may facilitate the identification of relevant information from the waveform, for example in comparison analysis. In contrast, in prior art methods, for example, even if a physician compared a waveform of a patient suspected of having asthma with a typical "asthma waveform", no reliable information would be obtained since not every waveform of an asthma patient show typical "asthma waveform shapes". A representative waveform of a patient suspected of having asthma, according to embodiment of the invention, would show the typical "asthma waveform shapes", if exist, and accordingly comparing such representative waveform with a typical "asthma waveform" would result in the relevant required information. As another example, prior art methods related to a slope of a waveform, however, one slope indicates a problem and the other slope may be normal, even if the patient does suffer from that problem. A representative waveform, according to embodiment of the invention, of a patient will show a slope which represents multiple waveforms and thus would yield the true information.

According to some embodiments of the invention, for comparison analysis, any number of representative waveforms may be compared to each other and/or presented simultaneously, to indicate a trend of the representative waveforms over time. For example, successive representative waveforms obtained over a period of time may be compared to each other and/or presented simultaneously, to indicate a trend of the representative waveforms over time. As another example, a selected set of representative waveforms taken every predetermined period of time (for example, every 30 minutes, every hour, three times a day or any other periods) may be compared to each other and/or presented simultaneously, to indicate a trend over time. The trend may be presented as a graph or table that demonstrates the change of one or more characteristics of the representative waveforms over time. A trend of parameters (such as scale factors and/or shape factors) may also be calculated and optionally displayed.

According to some embodiments of the invention, there is further provided a calculation and optionally a display of a confidence index (may also be referred to as a confidence level or level of confidence). The confidence index may be presented graphically or as value(s) and can relate to, for example, how many artifacts were removed, a dispersion of the shape(s) making up the representative waveform, how much averaging was performed and other features.

According to some embodiments of the invention, the methods disclosed herein allow an efficient storage of information. Firstly, a period of time and/or a number of waveforms can be defined by just one representative waveform and secondly, this representative waveform can be described by only several shape factors and size parameters. This can be regarded as a "double saving" which reduces the quantity of information required to define all the different waveforms by orders of magnitude (for example at least 5 orders of magnitude). Thus, the history of a subject may be saved and it is also possible to scan through the history even with basic monitors. According to some embodiments of the invention, in cases where a new waveform is not detected for a period of time (for example 10 seconds or any other period of time) in the real-time waveform (which indicates that there is a possible apnea event pending), then a time count or a similar indication may be added to the representative waveform or even replace it, to prevent a misleading presentation that would continue to show a representative waveform, while the subject is entering apnea.

According to some embodiments of the invention, any analysis of the representative waveform, for example, a comparison analysis as described herein, may be followed by providing medical recommendation(s). For example, for a sedated patient, when comparison of the representative waveform to previous representative waveforms shows deterioration in the patient's condition, a medical recommendation may include lowering the dosage and/or calling the doctor. As another example, for an intubated patient when the waveforms of a selected set of representative waveforms taken every predetermined period of time (for example, every 30 minutes) are compared to each other and indicate a trend of deterioration, a medical recommendation may include calling the doctor, changing treatment parameters, changing position of the patient, changing respiration parameters and other recommendations.

The representative waveform(s) and/or any display relating to the representative waveform(s) may be produced automatically (for example, updated every predetermined period of time) or per demand of a user ("on request").

The term "waveform" as referred to herein may include, according to some embodiments, a complete waveform or any sub-segment or combination of sub-segments of a waveform.

The terms "patient" and "subject" as referred to herein may be used interchangeably.

According to some embodiments of the invention, there is provided a method for producing a representative $CO_2$ waveform, the method comprising obtaining two or more $CO_2$ waveforms, for each of the two or more $CO_2$ waveforms determining one or more scale factors and one or more shape factors, computing, based on the one or more shape and scale factors of each of the two or more $CO_2$ waveforms, a representative set of shape factors and scale factors representing the two or more $CO_2$ waveforms and constructing a representative waveform based on the representative set of shape and scale factors. The two or more $CO_2$ waveforms may by complete waveforms or waveform sub-segments.

The determination of one or more scale factors may be based on normalization, for example, to 1 or to a maximal value. The one or more scale factors may include heights, widths and the like. The one or more shape factors may be determined by identifying parameters of best fit functions for each of the two or more $CO_2$ waveforms.

According to some embodiments, computing the representative set of shape factors may include collecting and averaging (for example weighted averaging) the parameters of the best fit functions.

According to some embodiments, constructing the representative waveform may include constructing a waveform based on the averaged parameters and back scaling.

According to some embodiments, the method for producing a representative $CO_2$ waveform may further include sub-segmenting each of the two or more $CO_2$ waveforms prior to determining one or more scale factors and one or more shape factors and constructing the representative waveform further includes combining the sub-segments of the representative waveform.

According to some embodiments, determining the one or more shape factors comprises converting each of the two or more $CO_2$ waveforms into an independent binary digital matrix, wherein a value of one (1) defines a position in the digital matrix where the waveform passes through and any other position of the digital matrix gets a value of zero (0). Determining the one or more shape factors may further include identifying a best fit function for each of the two or more independent digital matrices.

Computing the representative set of shape factors may include creating a summed matrix by summing the two or more independent digital matrices. Computing the representative set of shape factors may further include identifying the digital path which passes through positions having the highest values in the summed matrix. Computing the representative set of shape factors may further include identifying parameters of a best fit function for the digital path.

Constructing the representative waveform may include constructing a waveform based on the parameters of the best fit function. Constructing the representative waveform may further include back scaling.

According to some embodiments, the method may further include, prior to determining one or more scale factors and one or more shape factors, identifying artifacts in the two or more $CO_2$ waveforms and removing waveforms having artifacts.

According to some embodiments, the method may further include, prior to determining one or more scale factors and one or more shape factors, identifying unique patterns in the two or more $CO_2$ waveforms and removing at least a part of the unique patterns if identified. Constructing a representative waveform may further include superimposing the removed unique patterns or any representation thereof.

According to some embodiments, the method may further include, comparing the representative waveform to library of waveforms which are indicative of known medical conditions.

According to some embodiments, the method may further include, displaying the representative waveform. The representative waveform may be displayed starting from a predetermined point in the breath cycle. The method may further include, displaying the representative waveform over one or more representative waveforms. The method may further include, displaying the representative waveform over a baseline waveform. The method may further include, displaying the representative waveform over a textbook waveform. The method may further include, displaying the representative waveform with indication of the normal ranges. The method may further include, displaying multiple representative waveforms to show a trend over time. The multiplicity of representative waveforms may be displayed starting from the same predetermined point in the breath cycle. Alternatively, the multiplicity of representative waveforms may displayed in succession, such that one representative waveform starts at the point where another representative waveform ends.

According to some embodiments, the method may further include, updating the representative waveform every preselected period of time and/or every preselected number of waveforms. A rate of the update may be dynamically changeable base on measured or calculated parameter or an indication from a user.

According to some embodiments, the method may further include, providing a confidence index indicative of the reliability of the representative waveform. The method may further include, providing information regarding the representative waveform. The information may include linear slope, non-linear fit parameter, End-Tidal Carbon Dioxide, ($EtCO_2$), I to E (Inhalation to Exhalation) ratio or any combination thereof.

According to some embodiments, obtaining two or more $CO_2$ waveforms may include continuously monitoring a subject's breathing and collecting $CO_2$ waveforms from a subject. According to some embodiments, the method may further include, providing an indication of suspected apnea when a new waveform is not detected for a predetermined period of time.

According to some embodiments of the invention, there is provided an apparatus for producing a representative waveform, the apparatus comprising a control logic adapted to obtain two or more $CO_2$ waveforms, for each of the two or more $CO_2$ waveforms determine one or more scale factors and one or more shape factors, compute, based on the one or more shape and scale factors of each of the two or more $CO_2$ waveforms, a representative set of shape factors and scale factors representing the two or more $CO_2$ waveforms, and construct a representative waveform based on the representative set of shape and scale factors. The two or more $CO_2$ waveforms may by complete waveforms or waveform sub-segments.

The determination of one or more scale factors may be based on normalization, for example, to 1 or to a maximal value. The one or more scale factors may include heights, widths and the like. The one or more shape factors may be determined by identifying parameters of best fit functions for each of the two or more $CO_2$ waveforms.

According to some embodiments, computing the representative set of shape factors may include collecting and averaging (for example weighted averaging) the parameters of the best fit functions.

According to some embodiments, constructing the representative waveform may include constructing a waveform based on the averaged parameters and back scaling.

According to some embodiments, the control logic may further be adapted to sub-segment each of the two or more $CO_2$ waveforms prior to determining one or more scale factors and one or more shape factors and wherein constructing the representative waveform further comprises combining the sub-segments of the representative waveform.

According to some embodiments, determining the one or more shape factors may include converting each of the two or more $CO_2$ waveforms into an independent binary digital matrix, wherein a value of one (1) defines a position in the digital matrix where the waveform passes through and any other position of the digital matrix gets a value of zero (0). According to some embodiments, the control logic may further be adapted to identify a best fit function for each of the two or more independent digital matrices. According to some embodiments, computing the representative set of shape factors may include creating a summed matrix by summing the two or more independent digital matrices. Computing the representative set of shape factors further comprises identifying the digital path which passes through positions having the highest values in the summed matrix. Computing the representative set of shape factors may further include identifying parameters of a best fit function for the digital path.

According to some embodiments, constructing the representative waveform may include constructing a waveform based on the parameters of the best fit function and back scaling.

According to some embodiments, the control logic may further be adapted to, prior to determining one or more scale factors and one or more shape factors, identify artifacts in the two or more $CO_2$ waveforms and remove waveforms having artifacts.

According to some embodiments, the control logic may further be adapted to, prior to determining one or more scale factors and one or more shape factors, identify unique patterns in the two or more $CO_2$ waveforms and remove at least a part of the unique patterns if identified. Constructing a representative waveform may further include superimposing the removed unique patterns or any representation thereof.

According to some embodiments, the control logic may further be adapted to compare the representative waveform to library of waveforms which are indicative of known medical conditions.

According to some embodiments, the apparatus may further include a display unit adapted to display the representative waveform. The representative waveform may be displayed starting from a predetermined point in the breath cycle. The representative waveform may be displayed such that it is anchored to a certain position on the monitor (for example, at the corner of a monitor).

According to some embodiments, the apparatus may further include a display unit adapted to display the representative waveform over one or more representative waveforms. According to some embodiments, the apparatus may further include a display unit adapted to display the representative waveform over a baseline waveform. According to some embodiments, the apparatus may further include a display unit adapted to display the representative waveform over a textbook waveform. According to some embodiments, the apparatus may further include a display unit adapted to display the representative waveform with indication of the normal ranges. According to some embodiments, the apparatus may further include a display unit adapted to display a multiplicity of representative waveforms to show a trend over time. The multiplicity of representative waveforms may be displayed starting from the same predetermined point in the breath cycle. The multiplicity of representative waveforms may be displayed in succession, such that one representative waveform starts at the point where another representative waveform ends. The display unit may be adapted to update the representative waveform every preselected period of time and/or every preselected number of waveforms. A rate of the update may be dynamically changeable base on measured or calculated parameter or an indication from a user.

According to some embodiments, the control logic is further adapted to provide a confidence index indicative of the reliability of the representative waveform. The apparatus may further be adapted to continuously monitor a subject's breathing and collect $CO_2$ waveforms from a subject. The apparatus may further be adapted to provide an indication of suspected apnea when a new waveform is not detected for a predetermined period of time.

According to some embodiments of the invention, there is provided system for producing a representative waveform, the system comprising a control logic adapted to obtain two or more $CO_2$ waveforms, for each of the two or more $CO_2$ waveforms determine one or more scale factors and one or more shape factors, compute, based on the one or more shape and scale factors of each of the two or more $CO_2$ waveforms, a representative set of shape factors and scale factors representing the two or more $CO_2$ waveforms, and construct a representative waveform based on the representative set of shape and scale factors, and a monitor adapted to display the representative waveform.

BRIEF DESCRIPTION OF FIGURES

Examples illustrative of embodiments of the invention are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures (FIGS.) are listed below.

FIG. 4B schematically shows the same area as in FIG. 4A representing the normal range of $CO_2$ waveforms for a healthy subject and a representative waveform of an asthma patient, according to some embodiments of the;

DETAILED DESCRIPTION OF EMBODIMENTS

In the following description, various aspects of the invention will be described. For the purpose of explanation, specific configurations and details are set forth in order to provide a thorough understanding of the techniques. However, it will also be apparent to one skilled in the art that the techniques may be practiced without specific details being presented herein. Furthermore, well-known features may be omitted or simplified in order not to obscure the description(s) of the techniques.

Figure 1:
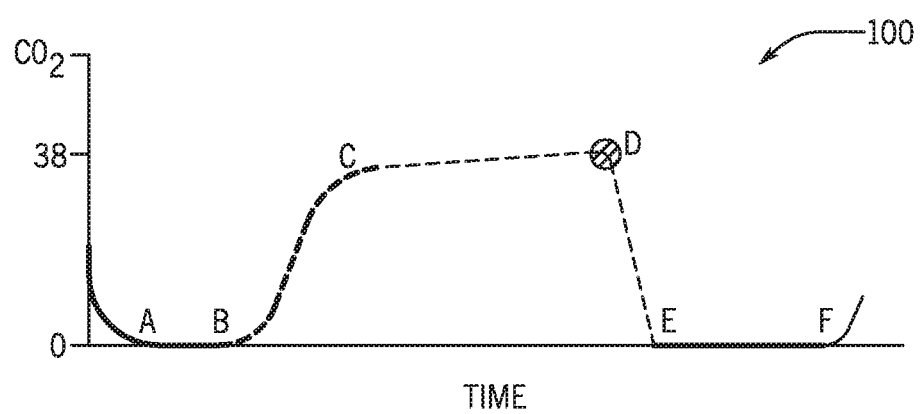
FIG. 1 schematically shows a "normal" (textbook) $CO_2$ waveform.

Reference is now made to FIG. 1 which shows a "normal" (textbook) $CO_2$ waveform (capnogram). Curve 100 represents the varying $CO_2$ levels throughout the respiratory cycle. Points A, B, C, D, E and F are depicted on the capnogram. Section (A-B) represents the end of inspiration (Phase I), where the $CO_2$ level is zero. Point B represents the beginning of exhalation. The sharp upstroke (B-C) represents the exhalation (Phase II). Follows is a gradual rise (C-D) (Phase III), a plateau having a peak just before (D) which represents the end of exhalation. The sharp downstroke back to zero (D-E) represents the inspiration (Phase IV) and is followed by a clean inspiration period (section E-F).

Figure 2A:
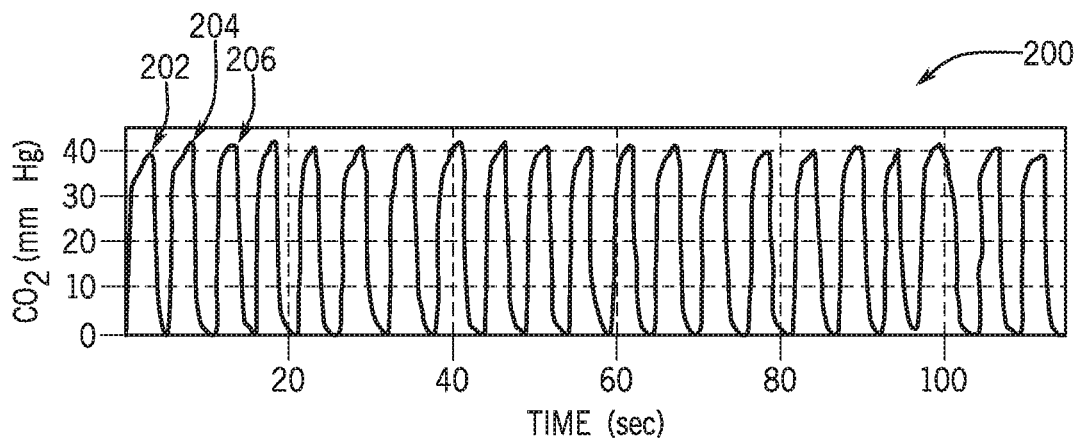
FIG. 2A schematically shows a measured capnogram which includes a series of successive $CO_2$ waveforms.
Figure 2B:
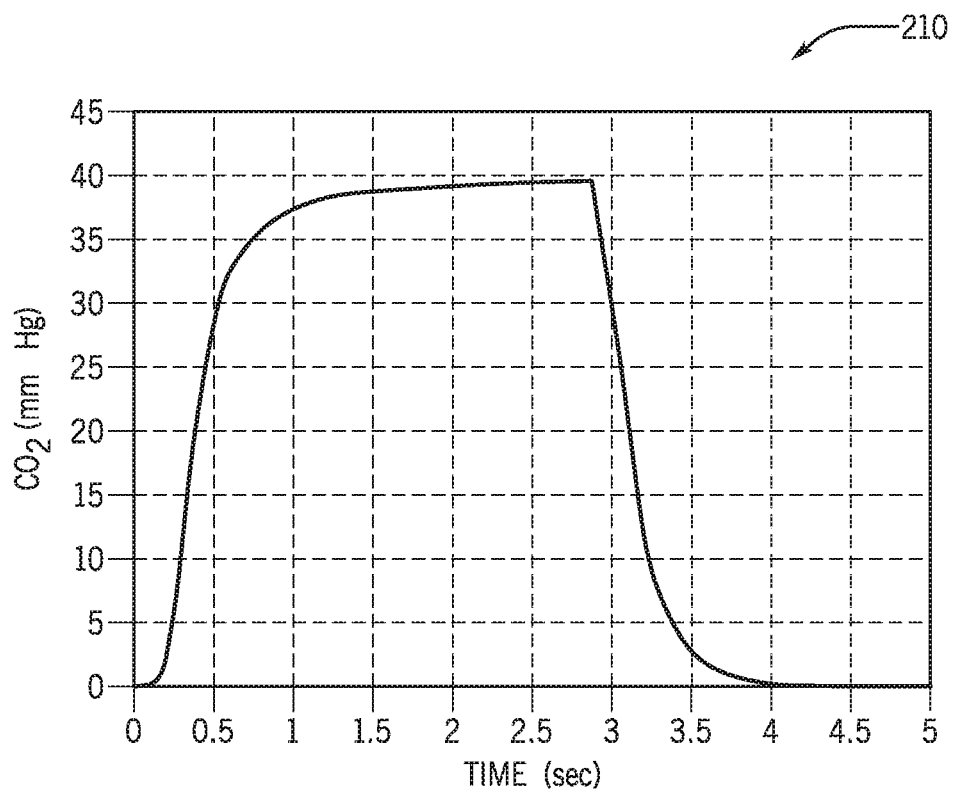
FIG. 2B shows one representative waveform that represents all successive $CO_2$ waveforms shown in FIG. 2A, according to some embodiments of the invention.

Reference is now made to FIG. 2A which shows a measured capnogram 200 which includes a series of twenty one (21) successive $CO_2$ waveforms (for example, 202, 204 and 206). It can be seen that each of the waveform is slightly different from the others both in shape and scale factors. Therefore, obtaining valuable information from such capnogram, particularly just from looking at it, may be very hard if not impossible. FIG. 2B schematically shows one representative waveform 210 that represents all twenty one (21) successive $CO_2$ waveforms shown in FIG. 2A, in accordance with some embodiments of the invention. This representative waveform is anchored to a corner (zero), not running across the screen and can change every X number of breaths or every Y number of seconds. A user (such as a doctor or a nurse) can easily obtain information from looking at the representative waveform, according to some embodiments of the invention. The scope of this invention, according to some embodiments, covers any method for displaying a representative waveform, such that it is anchored to a certain position in the monitor, such as a corner of the display.

Figure 3A:
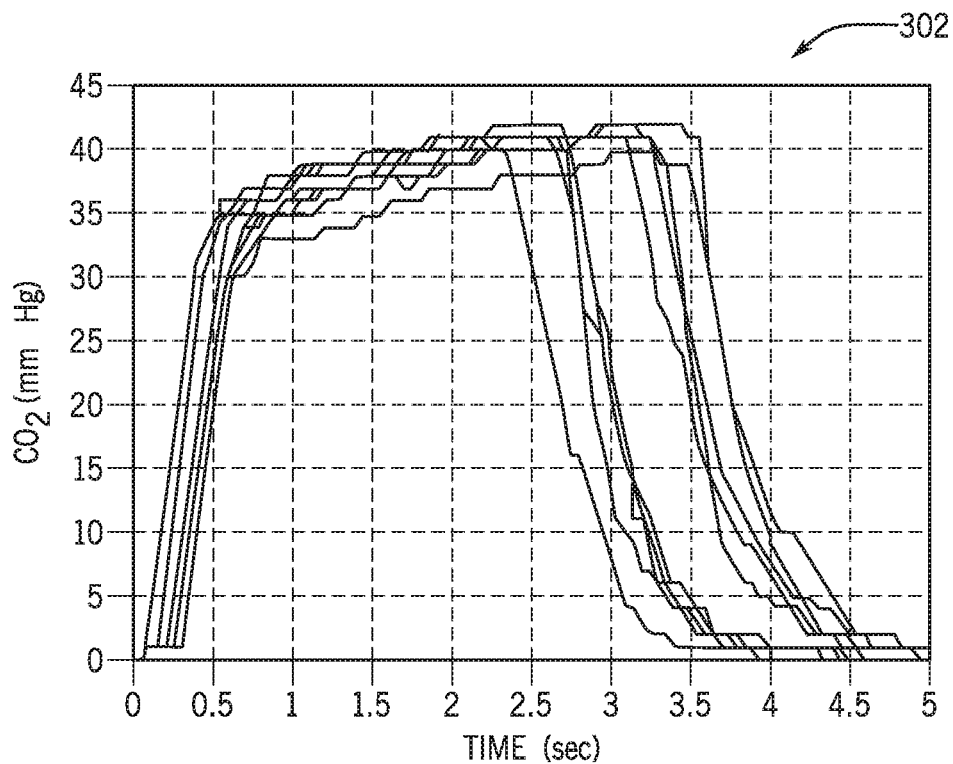
FIG. 3A shows a series of $CO_2$ waveforms presented on top of each other and a representative waveform that represents all $CO_2$ waveforms, according to some embodiments of the invention.
Figure 3B:
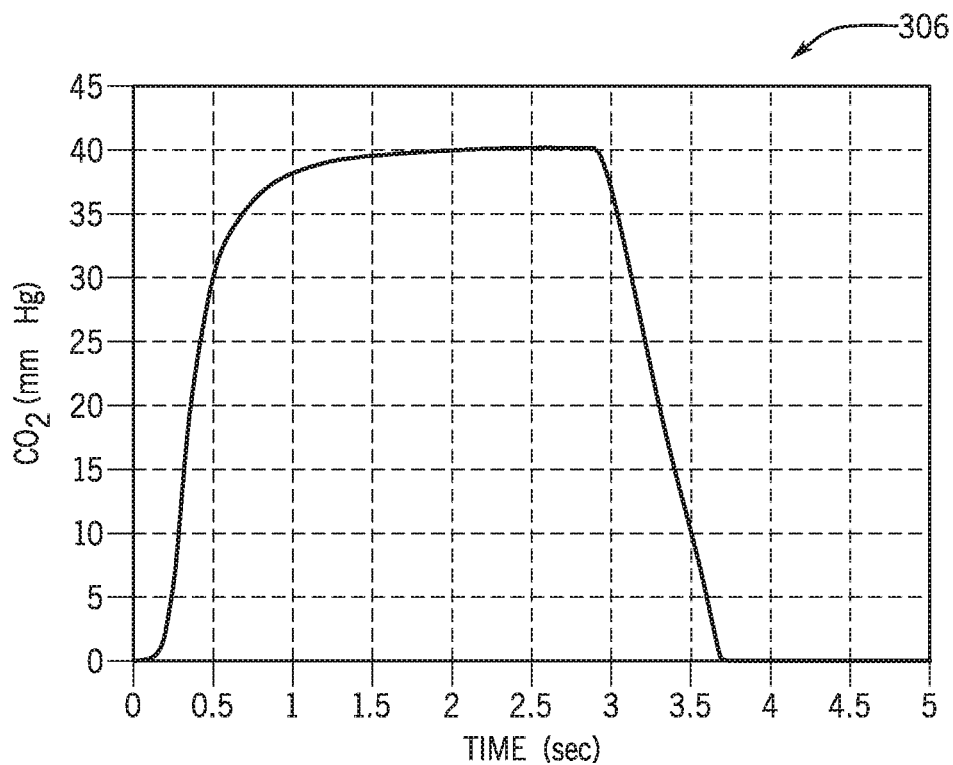
FIG. 3B shows a representative waveform that represents all $CO_2$ waveforms of FIG. 3A, according to some embodiments of the invention.

Reference is now made to FIG. 3A, showing an example of series of $CO_2$ waveforms 302, and to FIG. 3B which shows representative waveform 306, which represents all $CO_2$ waveforms 302 of FIG. 3A, according to some embodiments of the invention. As seen from FIG. 3A, obtaining any valuable information from looking at the multiplicity of the $CO_2$ waveforms 302, is much more complicated than from the single, clear representative waveform 306.

Figure 4A:
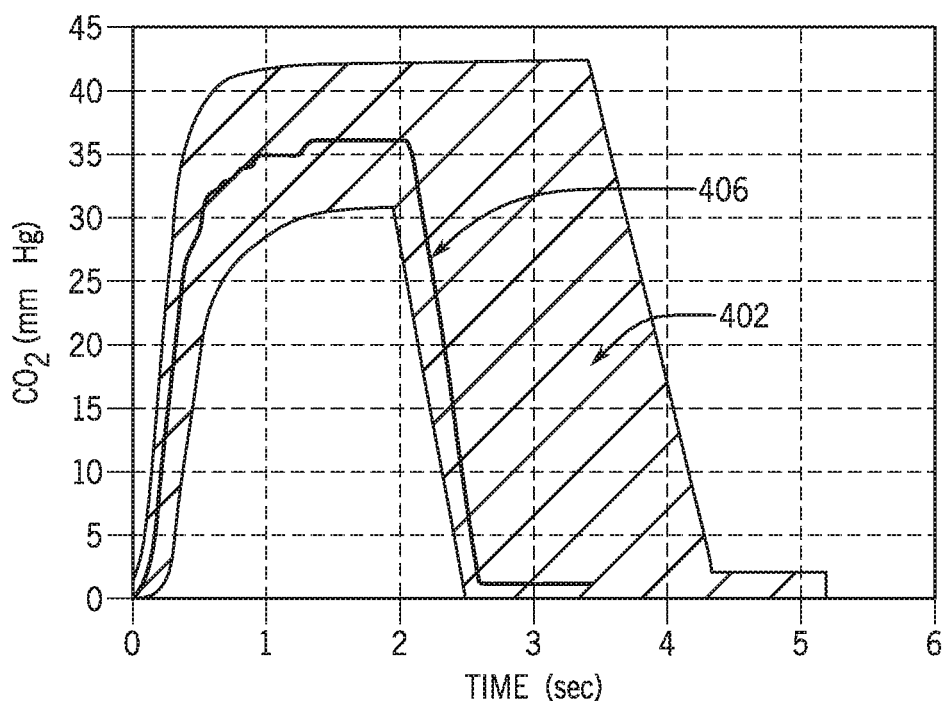
FIG. 4A schematically shows an area representing the normal range of $CO_2$ waveforms for a healthy subject and a representative waveform, according to some embodiments of the invention.
Figure 4B:
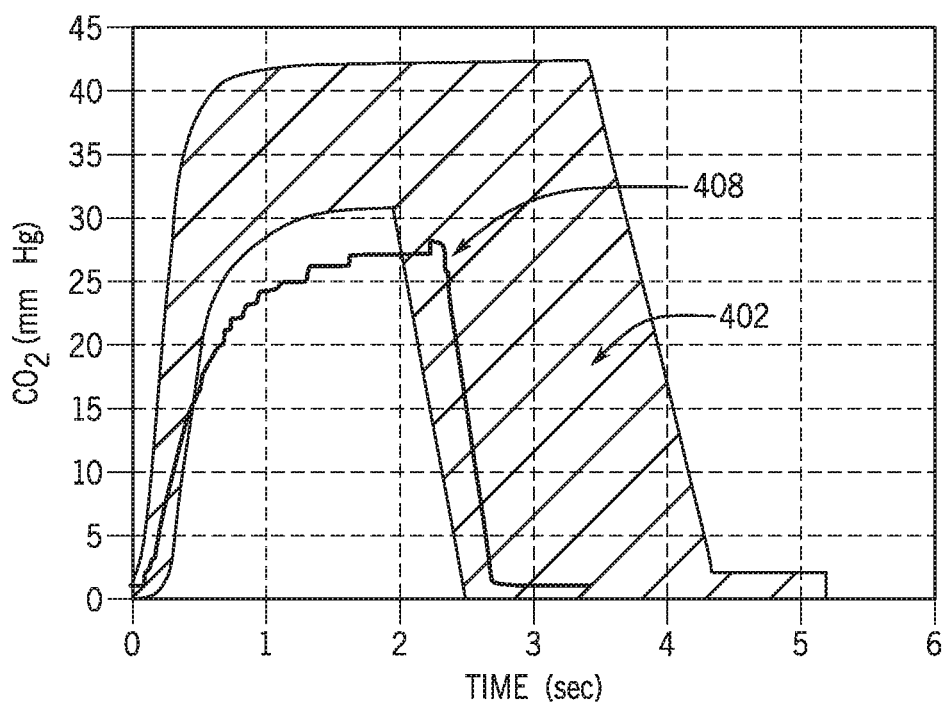

Reference is now made to FIG. 4A, which schematically shows an area 402 representing the normal range of $CO_2$ waveforms for a healthy subject and a representative waveform 406 (reconstructed from the last 16 breathes) of a healthy subject, according to some embodiments of the invention. FIG. 4B schematically shows the same area 402 representing the normal range of $CO_2$ waveforms for a healthy subject and a representative waveform 408 of an asthma patient (reconstructed from the last 16 breathes), according to some embodiments of the invention. Such presentation allows a user to clearly see that the representative waveform 406 is well within the normal range while representative waveform 408 (of an asthma patient) is not in the normal range. It can also be seen, for example, that representative waveform 408 (of an asthma patient) is lower and the "shoulder" defined as point C in FIG. 1 is rounder as compared to representative waveform 406 (of a healthy subject).

Figure 5:
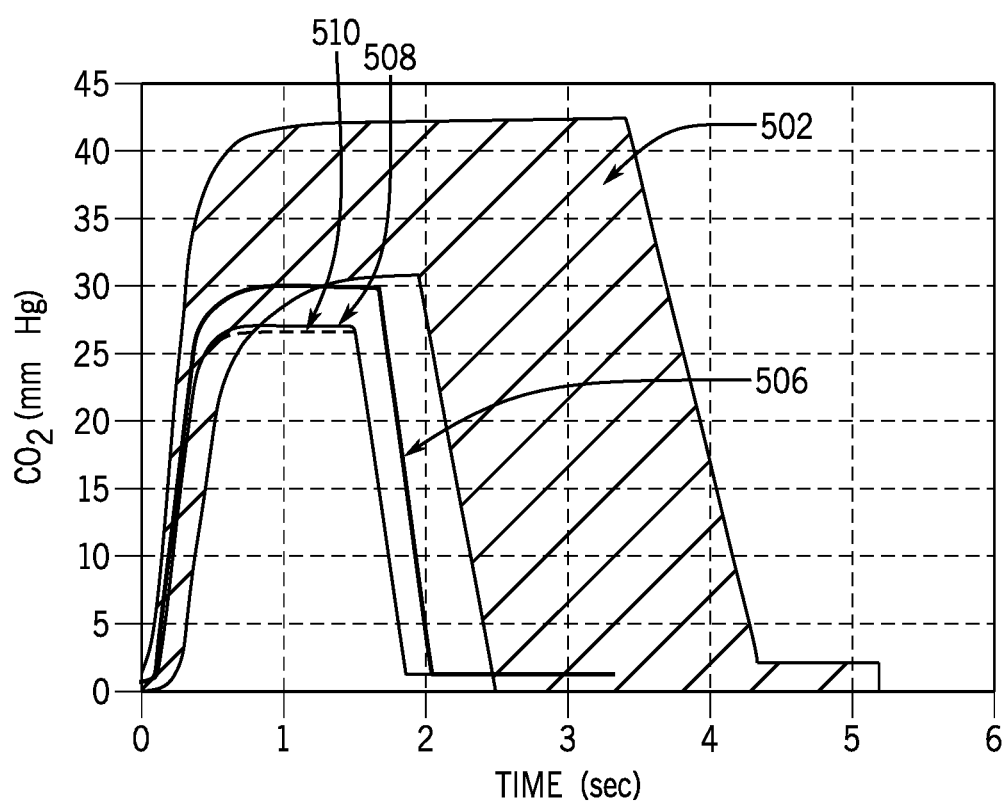
FIG. 5 schematically shows an area representing series of $CO_2$ waveforms and representative waveforms, according to some embodiments of the invention.

Reference is now made to FIG. 5, which schematically shows the last three representative waveforms 506, 508 and 510 of an asthma patient (each calculated every 16 breathes) presented over a background of an area 502 representing a "textbook" overall location of a series of $CO_2$ waveforms of a healthy patient, according to some embodiments of the invention. As seen from FIG. 5 it is clear to any user when looking at representative waveforms 506, 508 and 510 over the background of area 502, that the patient presenting representative waveforms 506, 508 and 510 has a breathing performance which is not normal. In addition, representative waveforms such as 506, 508 and 510 may represent a trend allowing a user to see changes of the patient condition over time.

It is noted that an area, such as area 502, representing a "textbook" (normal) overall location of a series of $CO_2$ waveforms of a healthy patient, may also be presented as two lines showing the upper limit and the lower limit of a normal range, as a collection of waveforms (as seen in FIG. 3A) or in any other way.

Producing (Constructing) a Representative Waveform

Figure 6A:
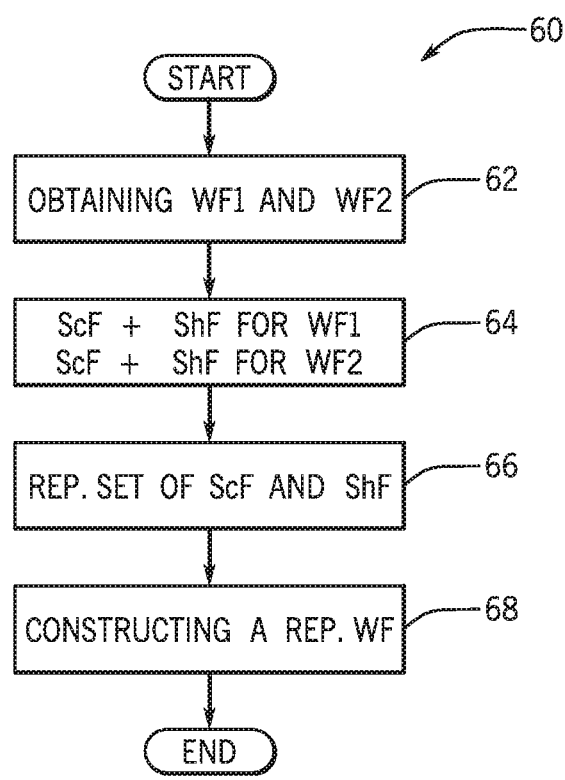
FIGS. 6A-B show a flow charts illustrating a process of producing (constructing) a representative waveform, according to some embodiments of the invention.

Reference is now made to FIG. 6A, which shows a flow chart 60 summarizing a process of producing (constructing) a representative waveform, according to some embodiments of the invention. Step 62 includes obtaining two or more waveforms. For the purpose of illustration, flow chart 60 refers to two waveforms (WF1 and WF2) but it is noted that any number of waveforms may be applied, for example, 5-20 waveforms, the number of waveforms detected in a period of time, such as 10-60 seconds or any other number of waveforms. Step 64 includes determining one or more scale factors (ScF) and one or more shape factors (ShF) for each of the two or more waveforms. Step 66 includes computing, based on the one or more shape and scale factors of each of the two or more waveforms, a representative (Rep) set of shape factors and scale factors representing the two or more waveforms (WF1 and WF2). Step 68 includes constructing a representative waveform (Rep WF) based on representative set of shape and scale factors one or more scale and shape factors.

Figure 6B:
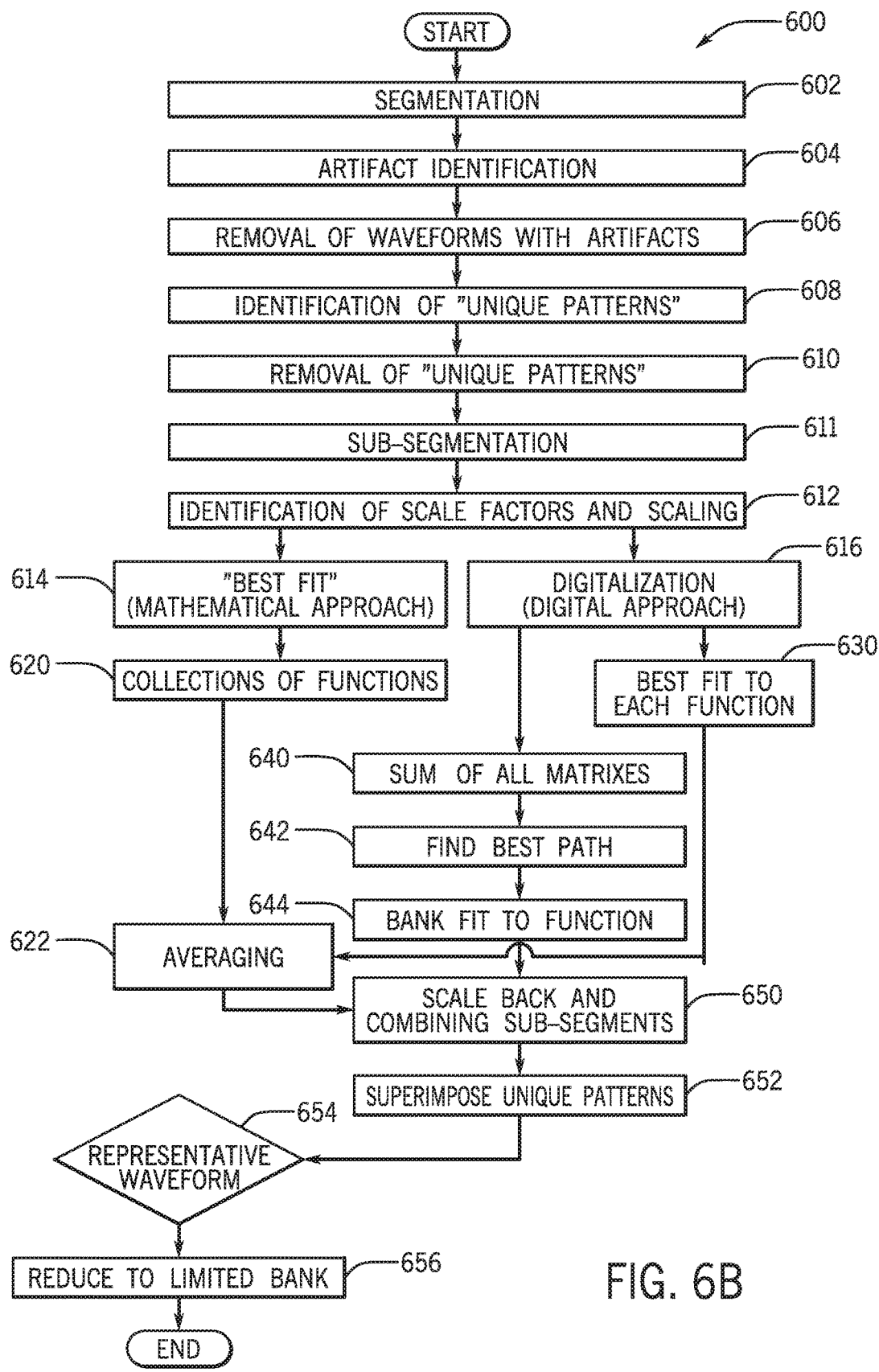
Figure 7A:
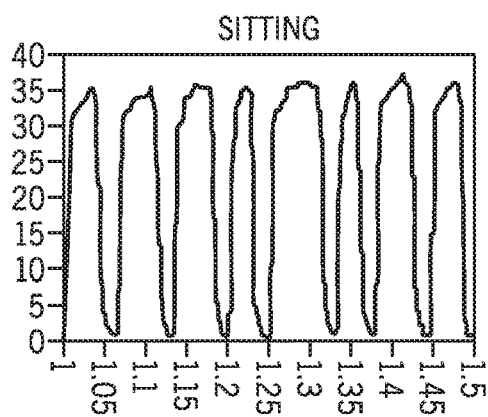
FIGS. 7A-F show $CO_2$ waveforms taken under different conditions, according to some embodiments of the invention.
Figure 7B:
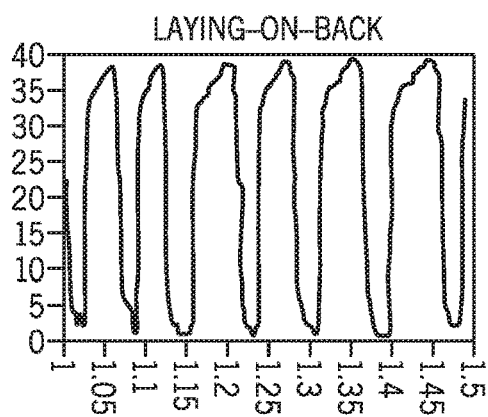
Figure 7C:
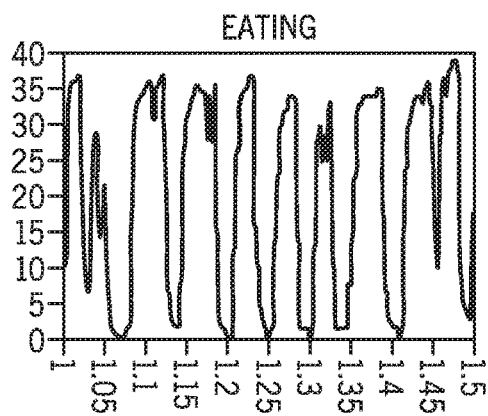
Figure 7D:
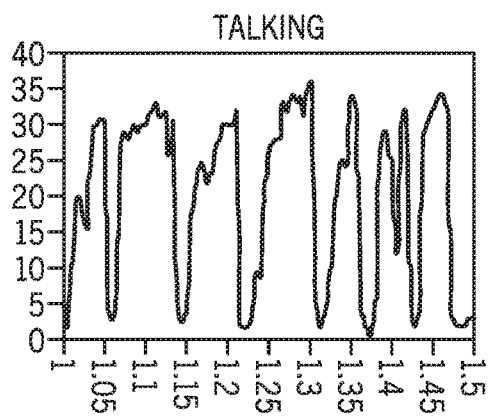
Figure 7E:
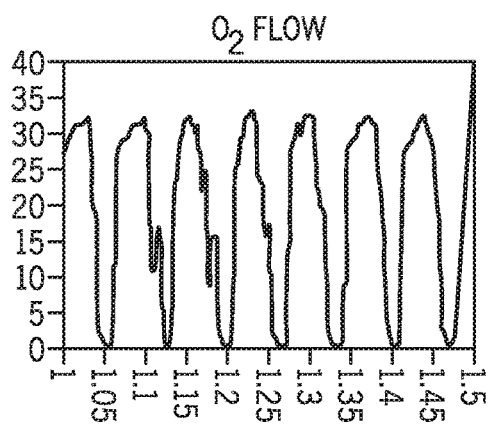
Figure 7F:
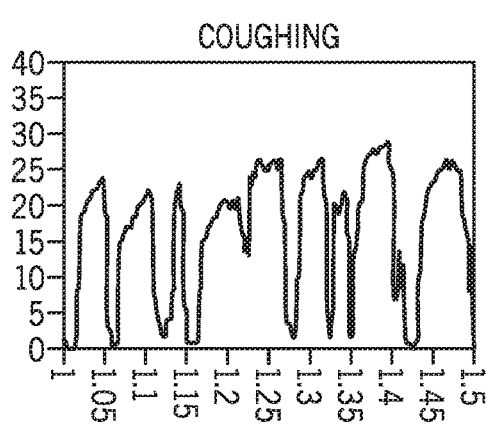

Reference is now made to FIG. 6B, which shows a flow chart 600 illustrating, in more detail, the process of producing (constructing) a representative waveform, according to some embodiments of the invention. When obtaining waveform(s) the first step 602 includes segmentation. Segmentation includes definition (beginning and end) of a single breath cycle (waveform) to be analyzed. A basic assumption may be that an anticipated waveform which would be received from a healthy subject would have a quasi-trapeze shape (see FIG. 1), with the four accepted identified stages (namely A-B, B-C, C-D, D-E and E-F). According to some embodiments, a received waveform that does not have one of these clear steps is considered as a breath without a shape that has clinical, physiological significance and hence is not used.

Step 604 includes artifact identification. There are many artifacts that can cause changes to waveforms and create difficulties to distinguish between patterns that have physiological importance and those that do not. An artifact may be defined, according to some embodiments, as a section of a waveform that has no clinical value. In many cases, artifacts do not originate from a medical condition and particularly do not originate from respiratory and cardiac physiology. Examples of artifacts may include notches and spikes caused by talking, coughing, drinking, eating, interference by an appliance such as a cell phone, a computer or the like. These artifacts are generally non-repetitive.

Other changes to the waveforms may be caused by regular activities, such as, moving, lying, sitting, changing a position and the like. These may optionally be treated as artifacts but may also be treated as different variations of waveforms and may still be regarded as "acceptable" data. Another effect that may cause changes to the waveform is the dilution of the breath sample with gasses, such as $O_2$, which are delivered to the subject. This type of effect generally changes the waveforms in a repetitive manner.

Methods are disclosed herein, in accordance with some embodiments, for eliminating or reducing the effect of artifacts. Artifacts may be identified based on predefined patterns that have been identified using controlled studies on both ill and healthy patients. They may further be identified, by their more ad-hoc appearance, shape and position in the waveform.

Examples of the effect of patient's activities and $O_2$ flow on waveforms can be seen in FIGS. 7A-F, which demonstrate waveforms of a patient taken during sitting, lying on the back, eating, talking, receiving $O_2$ flow, and coughing, respectively. By looking at FIGS. 7A-F it can be seen that a user may loose valuable information due to the masking effect of the artifacts that may hide the required and meaningful information. According to some embodiments, breath cycles (waveforms) with a measurable quantity of artifacts may be identified and removed from the set of waveforms used to reconstruct the representative waveforms.

Figure 8A:
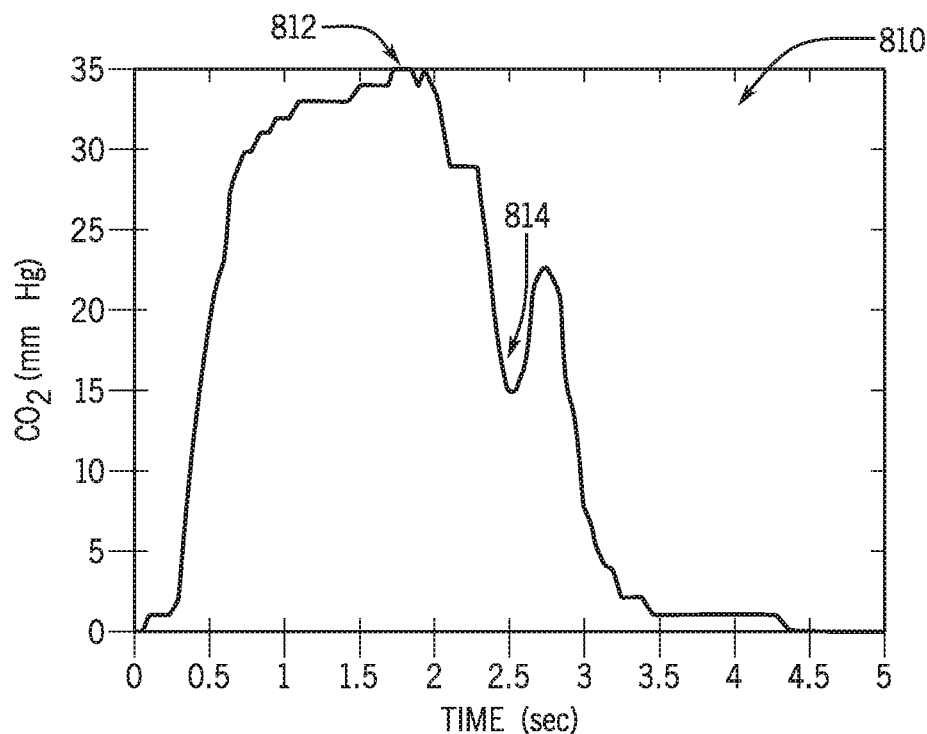
FIGS. 8A-B show $CO_2$ waveforms, according to some embodiments of the invention.
Figure 8B:
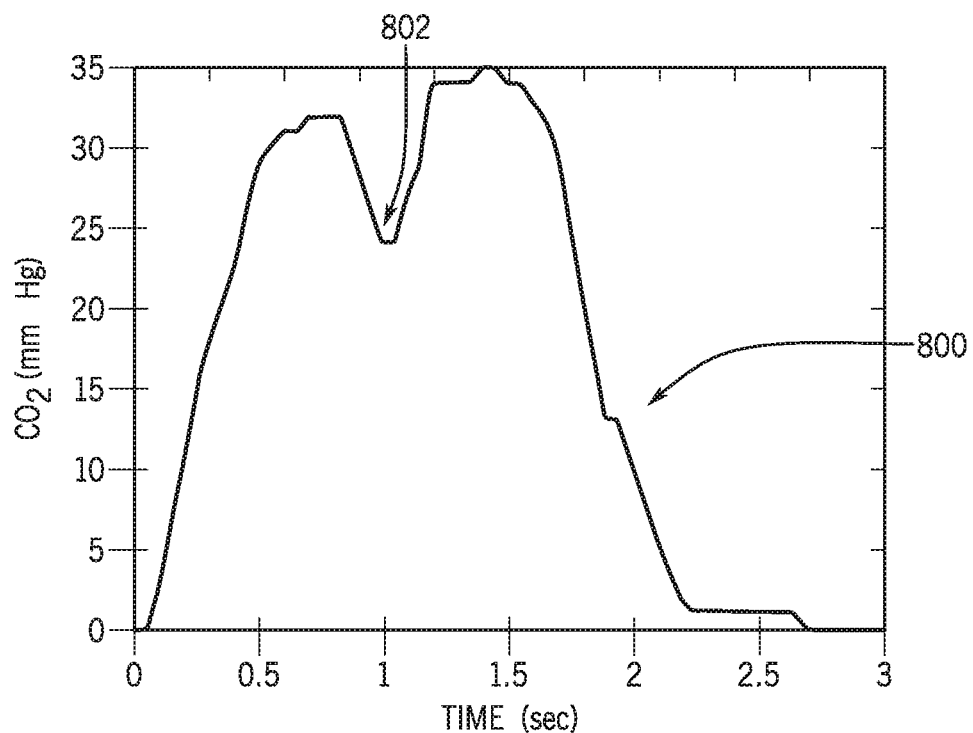

According to some embodiments, in order to define artifacts a dataset comprising well defined and labeled artifacts (such as the activities discussed in relation to FIGS. 7C,D and F) may be generated. According to some embodiments, among the features that discriminate between artifacts and regular waveform features are dips trend and depth and the fit to function (such as, the presence and trend of dips larger than a certain threshold during upstroke and the measure of fitness to a function, Mean Square Error, for example). For example, a mathematical definition of artifact may include a waveform with dips larger than 5 mmHg during upstroke or plateau or with mse of a logarithmic function>2. Down-stroke dips are generally not regarded as artifacts since they often occur with addition of oxygen flow. FIGS. 8A-B show $CO_2$ waveforms, according to some embodiments of the invention. Upstroke dip 802 having depth of approximately 8 mmHg can be seen in $CO_2$ waveform 800 in FIG. 8A. Two down-stroke dips 812 and 814 with depth 1 and 20 mmHg respectively can be seen in $CO_2$ waveform 810 in FIG. 8B. Upstroke dip 802 of $CO_2$ waveform 800 in FIG. 8A may represent an artifact, if it is not a frequent (repetitive) event.

Figure 9:
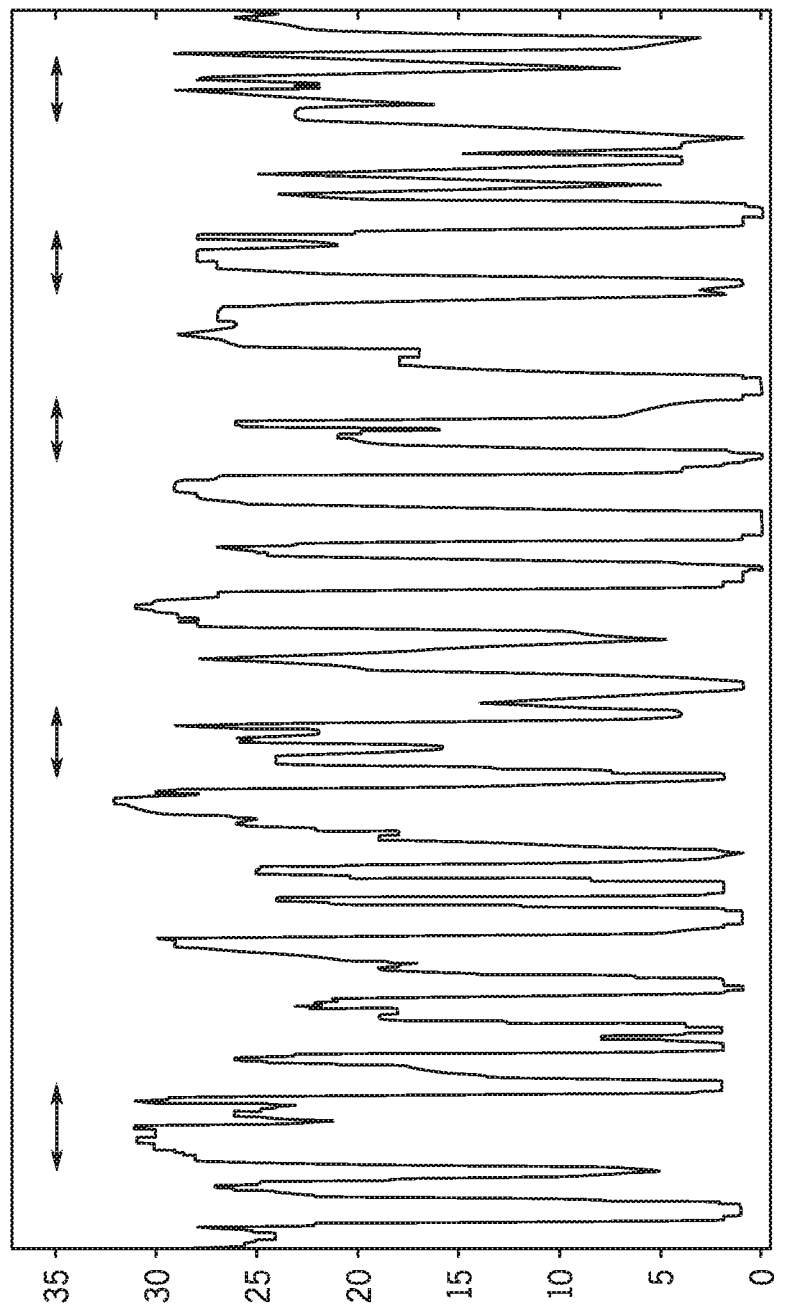
FIG. 9 shows $CO_2$ waveforms, according to some embodiments of the invention.

FIG. 9 shows a series of waveforms some of which (waveforms under the arrows) have significant artifacts. Waveforms having significant artifacts may be excluded from further analysis (see next step, step 604).

Returning to flow chart 600 of FIG. 6B, the next step after identifying artifacts (step 604) is step 606 which includes removal of waveforms with artifacts. According to some embodiments, these waveforms will not be used for further analysis. After this step, the waveforms are cleaned (or at least essentially cleaned) from artifacts, which as mentioned hereinabove, did not originate from a medical and physiological condition.

Figure 10A:
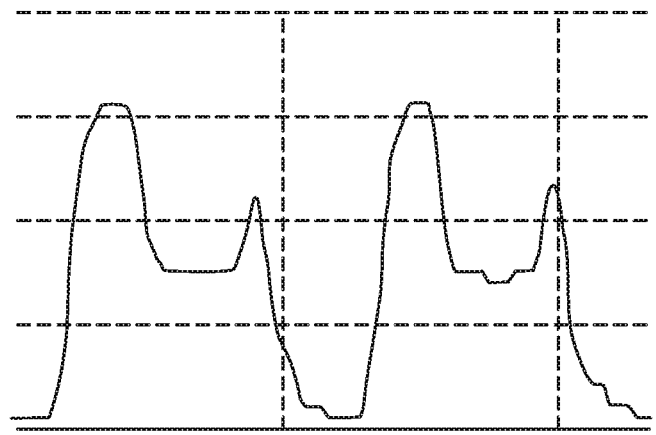
FIGS. 10A-B show $CO_2$ waveforms, according to some embodiments of the invention.
Figure 10B:
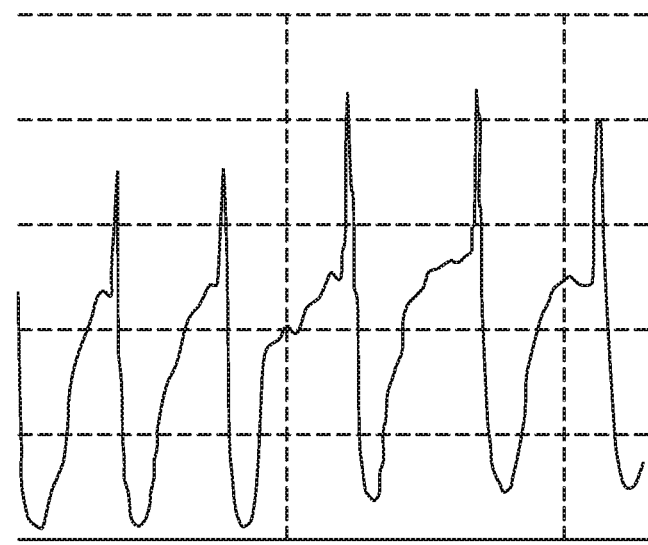

Step 608 includes identification of unique patterns (characters) which generally have clinical significance. These unique patterns are typically recurring patterns that are superimposed on the standard waveforms, having an essentially trapeze like shape. According to some embodiments, the term "recurring patterns" may refer to patterns that recur in X % of the waveforms, wherein X % can be over 10%, over 20%, over 30-50% or X can be any other percent which can be constant or vary before or during monitoring. These unique patterns may provide clinical information when analyzed based on predefined patterns learnt during clinical studies. FIGS. 10 A and B show, according to some embodiments, waveforms having reoccurring well-defined unique patterns, with seemingly physiological origins.

Returning to flow chart 600 of FIG. 6B, the next step after identification of unique patterns (step 608) is step 610, which include removal of the (recurring) unique patterns. According to some embodiments, these unique patterns are separated from the standard wave shape (standard/normal waveform) but are returned in a later stage of the process of waveform reconstruction (step 652).

Step 611 is optional and includes sub-segmentation of the waveform. As discussed above, segmentation (step 602) includes definition (beginning and end) of a single breath cycle (waveform) to be analyzed. Sub-segmentation (step 611) includes defining the "stages" of the waveform. As mentioned above, a basic assumption may be that an anticipated waveform which would be received from a healthy subject would have a quasi-trapeze shape (see FIG. 1), with the four accepted identified stages (namely A-B, B-C, C-D, D-E and E-F). A waveform could be divided into any number of stages, such as 1 (not dividing at all), 2, 3, or more. For example, as shown herein, according to some embodiments, the waveform is sub-segmented into two sub-segments. The first stage (sub-segment) relates to the increase in $CO_2$ stage, including both upstroke (section B-C in FIG. 1) and plateau (section C-D in FIG. 1). The second stage (sub-segment) relate to the decrease in $CO_2$, including the down-stroke (section D-E in FIG. 1) and the following clean inspiration period (section E-F in FIG. 1). These two stages (sub-segments) basically separate between initiation of exhalation up to the end of exhalation, and to the onset of inhalation up to the next initiation of exhalation.

In case optional step 611 was applied, the following steps of flow chart 600 may be done on each sub-segment of the waveform separately or on a combination of sub-segments. In case optional step 611 was not applied, the following steps of flow chart 600 may be done on a whole waveform (a single breath cycle) from its beginning to its end.

Step 612 includes identification of "scale factors" and scaling. Scale factors, as discussed hereinabove, refer to waveform values, such as, height, width, duty cycle, area under the curve or any other parameter or combination of parameters. Scaling may include, for example, normalization. Normalization may include for example, normalization of $CO_2$ value by dividing $CO_2$ by its maximum, such that the maximum value of $CO_2$ will always be 1.

The next steps of flow chart 600, which describes the process of producing (constructing) a representative waveform, relate to handling the waveforms "shape factors". Shape factors, as discussed hereinabove, refer to any parameter that relate to and/or describe the shape of a waveform. For example, parameters of a non-linear function describing the upstroke or the entire exhalation stage as portrayed by a waveform. The shape factors of the waveform(s) are generally indicative of physiological condition(s) of a patient. For example, dominant shape factors of the waveform(s) may relate to respiratory process such as the mechanics of breathing. At this point, flow chart 600 may split. According to some embodiments of the invention, construction of the representative waveform may be based on a "best fit" mathematical approach (step 614) and/or on digitization (digital approach) (step 616).

First Option (Step 614):

The "best fit" mathematical approach (step 614) may include initial characterization extraction based on given, predefined functions describing (fitting) a given waveform or sub-segment in a waveform, for example, one or two sub-segments of a two sub-segment waveform (as disclosed herein above, the first sub-segment may relate to the decrease in $CO_2$, including the upstroke (section B-C in FIG. 1) and plateau (section C-D in FIG. 1) and the second sub-segment may relate to the decrease in $CO_2$, including the down-stroke (section D-E in FIG. 1) and the following clean inspiration period (section E-F in FIG. 1)). For applying the "best fit", any known mathematical means of best fit may be used, such as "fit to function" or a look up table with limited best fit possibilities. Construction of the representative waveform can be realized for example, by choosing from a given limited number of possible, predefined shapes (based on "closest to") or by a "true" mathematical calculation of representative value(s) using predefined functions for this purpose. A mixture of both options can also be used, in other words, first calculating the "true" representative value(s) and then looking for its best fit.

Each waveform (and also the representative waveform) can thus be defined by a set of functions with their parameters (shape factors) and by other parameters (scale factors) which together build up the waveform. Hence the waveform obtained in the last "x" seconds or the "y" waveforms obtained can be memorized by defining just a few given parameters (shape factors and scale factors).

Figure 11:
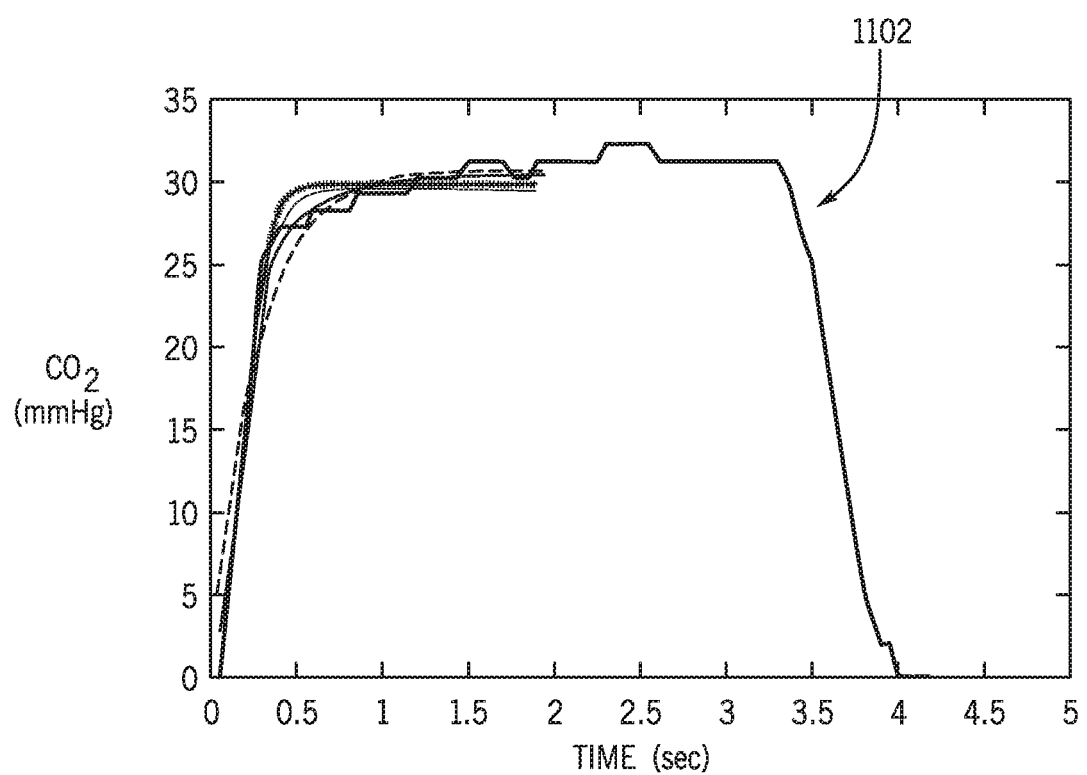
FIG. 11 shows $CO_2$ sample waveforms (taken from normal dataset) and their estimated fit with the five functions, according to some embodiments of the invention.
Figure 12:
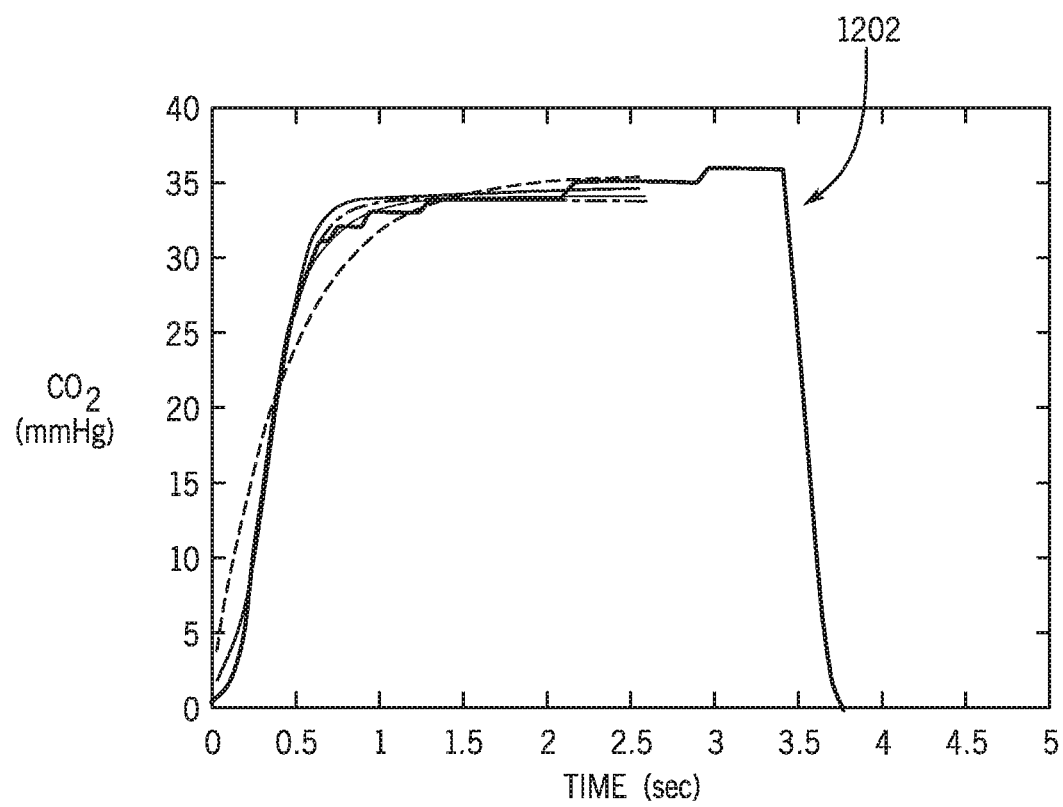
FIG. 12 shows $CO_2$ sample waveforms (taken from asthma patient dataset) and their estimated fit with the five functions, according to some embodiments of the invention.
Figure 13A:
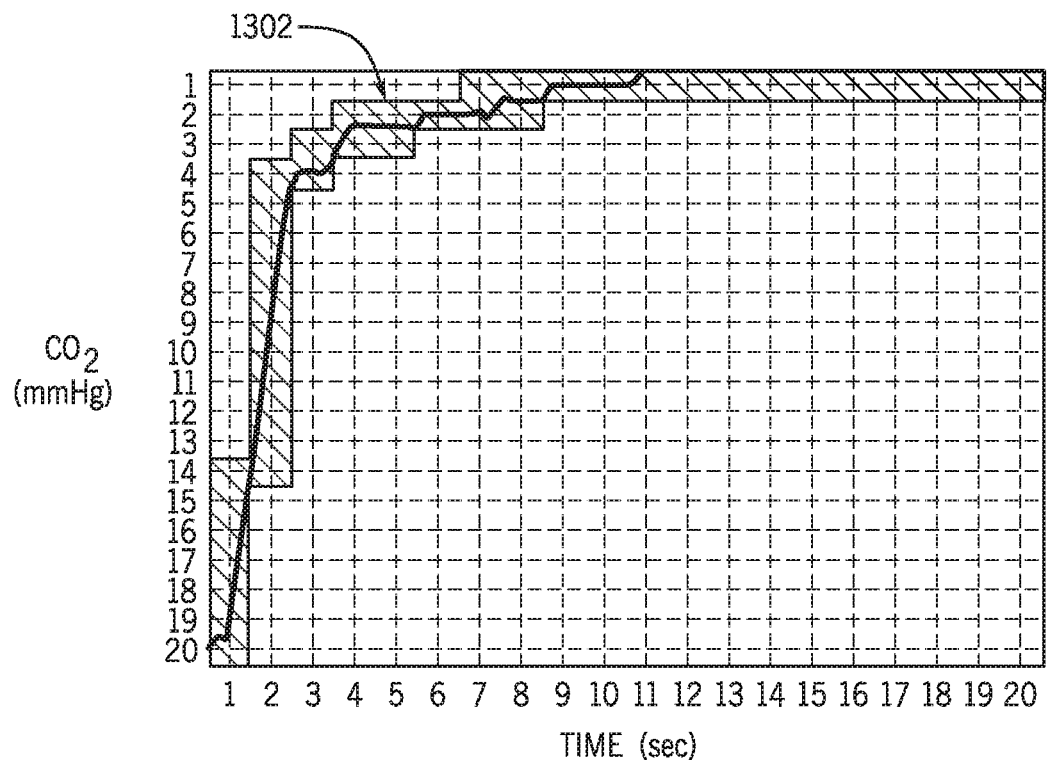
FIGS. 13 A, B, C, and D which show a grid-matrix (20×20) representation of waveform sub-segments, according to some embodiments of the invention.
Figure 13B:
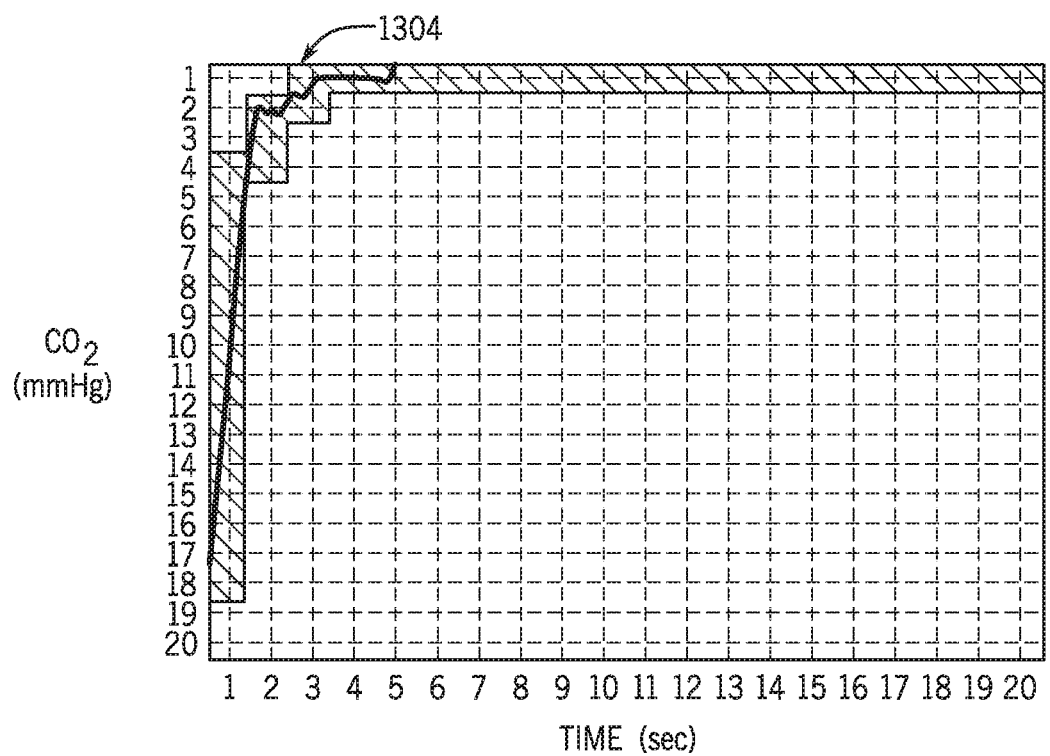
Figure 13C:
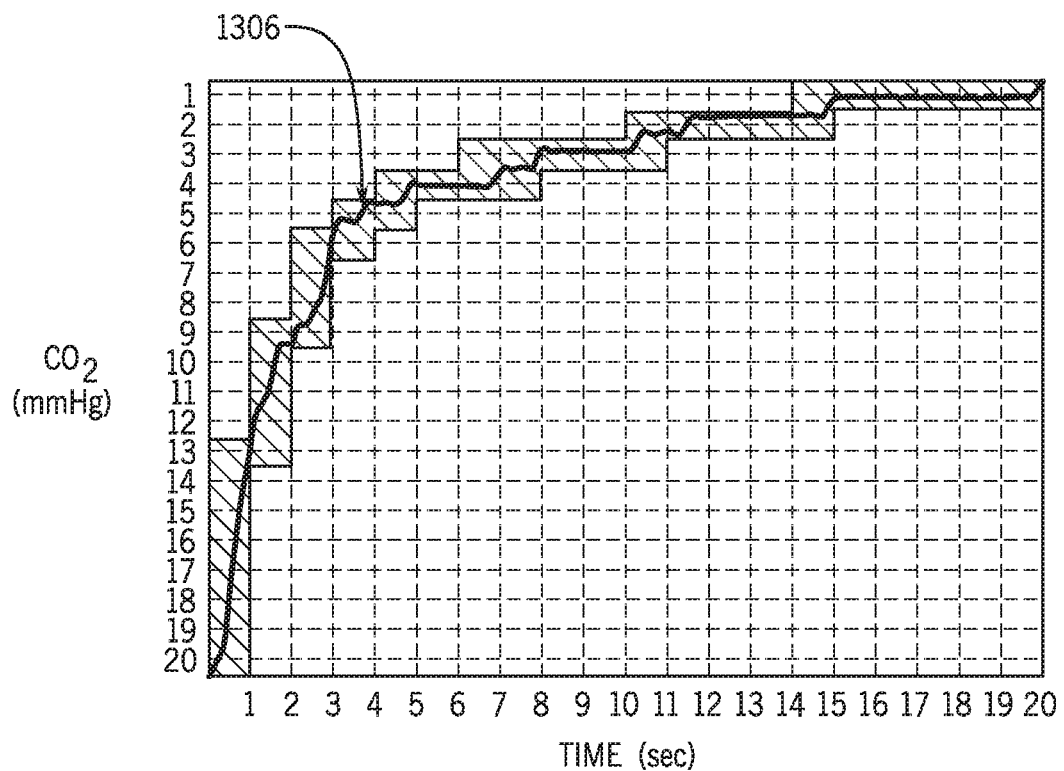
Figure 13D:
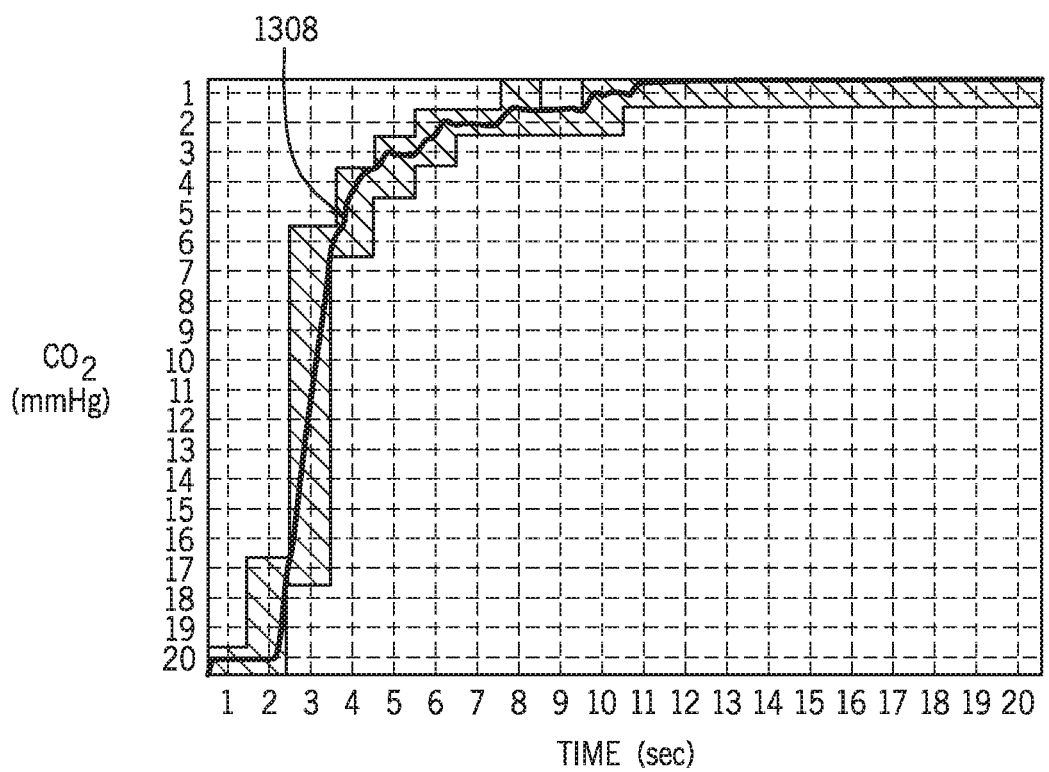

Reference is now made to FIG. 11, which shows a sample waveform 1 102 (taken from normal dataset) and its estimated fit with five functions. Reference is also made to FIG. 12, which shows sample waveforms 1202 (taken from asthma patient dataset) and its estimated fit with five functions. In each of FIGS. 11 and 12 only the first sub-segment of each wave form is shown with the "fit to function(s)" but of course the second sub-segment may also be processed to fit to any number of functions. It is also noted that each waveform can be divided to any number of sub-segments and each sub-segment or combination of sub-segments may be processed to fit to any number of functions out of which the best fit (for example, the function that is closest to the waveform curve) may be selected.

The functions shown in FIGS. 11 and 12 are the following (the function names are arbitrary):

$$1 - \text{Log} - piy = (1 + p3\blacksquare\exp(-/?1\cdot x))$$

$$2 -$$
$$GLC \text{ (generalized logistic curve): } \{1 + p4 - \exp(-\text{ph}(x - p5)))\mid /'')\rangle$$

$$3 - \text{Verhulst: } y\text{--}, \text{ where, } a = 1 + p\backslash-\exp(-x/p2);$$
$$b = 1 + p3\cdot\exp(-x/p2)b$$

$$A - \text{WeilbullCDF: } y = p3 - \{\backslash-\exp(-x/pi))''^2$$

$$5 - p15p: y = p1 + \frac{p5 - p1}{a}, \text{ where, } a = \left(1 + \left(\frac{x}{p2}\right)^{p3}\right)^{p4}$$

It is noted that any other function or combination of functions may be used and that the five functions presented herein are only exemplary functions.

Returning to flow chart 600 of FIG. 6B, the next step include collection of functions, step 620. This step includes collecting the parameters of the functions that describe each waveform. The next step, step 622, includes averaging these parameters (and/or using any linear or non-linear mathematical method/function, such as arithmetic mean, geometric mean, integration, median or any power mean) over "y" waveforms or over the waveforms obtained during "x" seconds. Averaging the parameters and/or using any linear or non-linear mathematical method/function may permit, for example, computation of the most dominant, or reoccurring, most representative parameters. Averaging may include using a weighted average. In addition, waveforms with parameters that are far from the mean may be removed or used with lower weighting.

This step results in obtaining the parameters of a representative normalized waveform or representative normalized waveform sub-segment(s) (when the waveform was sub-segmented first, such as in step 611).

As mentioned above, one can also use a given limited list of waveform shapes, and mathematics may be used to find a given waveform shape which is closest to the measured waveform. This way, it is possible to have a limited list of predefined possible waves, for simpler and faster calculations.

The next step, step 650, includes scale back and combining the representative normalized waveform sub-segments (if applicable). The parameters that were used to normalize may also be averaged, and used to return the representative normalized waveform back to the size that represents the true waveforms used to create it. This step results in a representative waveform that still lacks the recurring unique patterns which were removed step 610.

The next step, step 652, thus includes adding (superimposing) any recurring or dominant unique patterns which were previously removed (such as in step 610) to the representative waveform. These unique patterns may be saved and reconstructed from predefined shapes stored in the memory, but whose sizes are defined based on the collected waveforms. This step results in the final representative waveform 654.

Optional step 656 may include comparing the final representative waveform to library of waveforms which are indicative of known medical conditions (for example, typical abnormal waveforms). This may facilitate providing diagnosis, the degree of severity and/or medical recommendations.

Second Option (Step 616):

Returning to step 610 of flow chart 600 of FIG. 6B, instead of (or in some cases, in addition to) continuing to step 614 ("best fit" mathematical approach), the digital approach, step 616 (digitalization), may be selected. This step includes creating a low-resolution digital matrix to individually define the normalized waveforms. The matrix may be for example, a 20 by 20 or 50 by 50 matrix wherein a value of "1" defines a position where the wave passes through and "0" for other point.

Step 616 of flow chart 600 of FIG. 6B can be described, for example, by FIGS. 13 A, B and C which shows a binary grid-matrix (20×20) representation of waveform sub-segments 1302, 1304, 1306, respectively. The waveform sub-segments in FIGS. 13 A, B, C and D are the upstroke (exhalation) parts of whole breathing waveforms, but can be any other sub-segments or combinations of sub-segments. In each one of FIGS. 13 A, B, C and D, waveform sub-segments 1302, 1304, 1306 and 1308, respectively, were placed on a grid-matrix (shown as 20×20 squares, but of course it can be more or less, depending on the resolution required, the more squares the better the resolution). Every square through which waveform sub-segments of 1302, 1304, 1306 or 1308 passes gets a value of one (1), while squares through which waveform sub-segments 1302, 1304, 1306 or 1308 do not passes get a value of zero (0).

After Step 616 of flow chart 600 of FIG. 6B two options are possible, option A (step 630 of flow chart 600 of FIG. 6B) and option B (step 640 of flow chart 600 of FIG. 6B).

Option a (Step 630 of Flow Chart 600 of FIG. 6B):

Step 630 includes comparing separate grid-matrices to a set of preselected functions of waveforms (function bank/database). In this step, a set of predefined functions are collected. These selected functions best describe the separated waveforms. The representative normalized waveform or representative normalized waveform segment(s) can then be found based on mathematical integration and/or weighting of the waveforms building up the set (by going to step 622).

Figure 14:
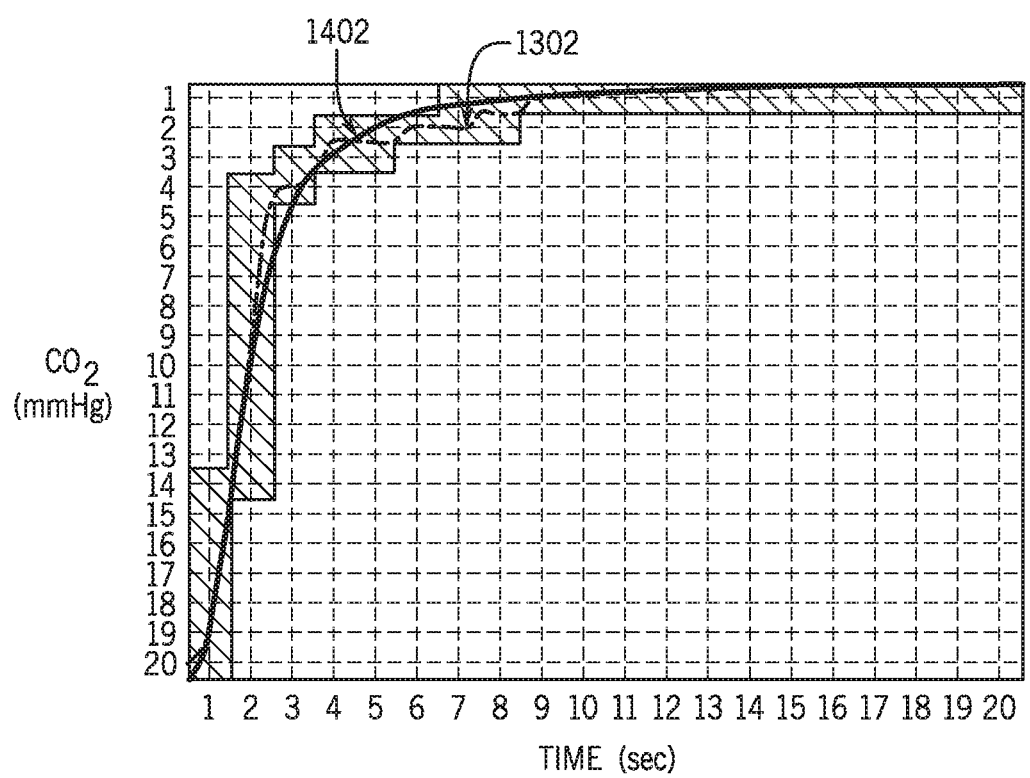
FIG. 14 shows a waveform sub-segment of FIG. 14 A on the binary grid-matrix (20×20) and its fit line, according to some embodiments of the invention.

FIG. 14 shows waveform sub-segment 1302 on the binary grid-matrix (20×20) of FIG. 13 A and its fit line 1402 (from a set of preselected functions of waveforms, function bank/database). Fit line 1402 best describes (fits) the grid-matrix's squares which received a value of 1 (through which waveform sub-segments of 1302 passed). Fit line 1402 in this example is number 20 from a database, with confidence level 0.84.

Option B (Step 640 of Flow Chart 600 of FIG. 6B):

Step 640 of flow chart 600 of FIG. 6B includes performing a mathematical combination (sum) of the digitized matrices to form a superimposed digitized matrix. Again, outlying waveforms may be removed.

After forming the superimposed (summed) digitized matrix (step 640), step 642 includes finding the best path or in other words, finding the most dominant digital path taken by the largest number of matrices (which represent the waveforms). This step also promotes removal of artifacts that were not attended to previously.

The following step 644 includes finding the best fit function to the superimposed (summed) digitized matrix (from a set of preselected functions of waveforms, function bank/database). This accelerates the computation and minimizes the data storage.

Figure 15:
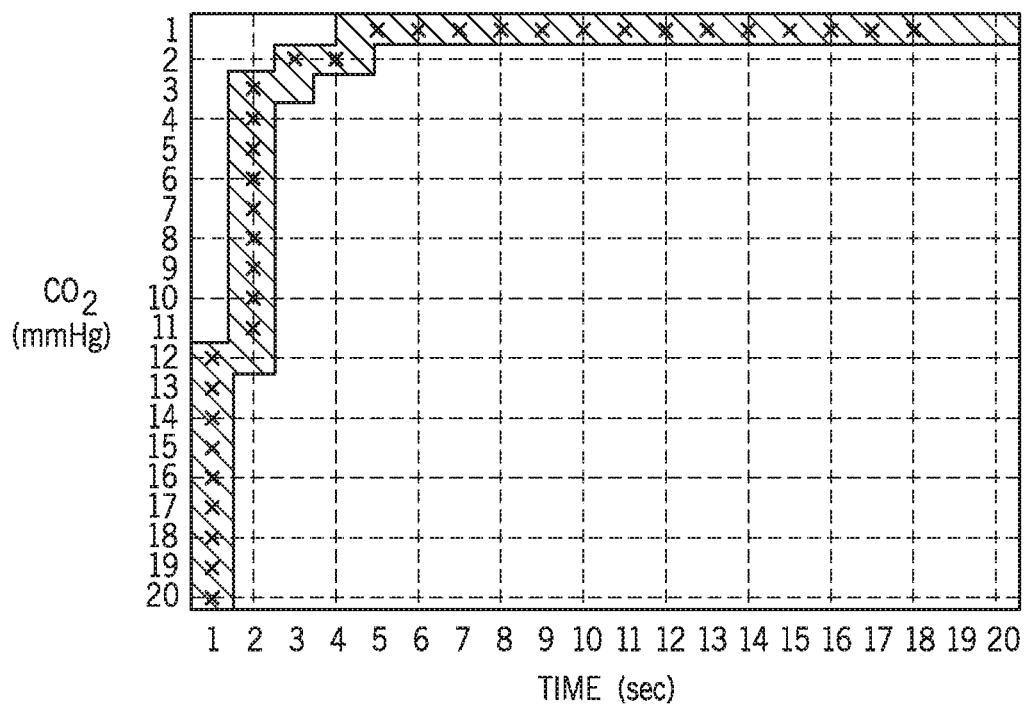
FIG. 15 shows a summed grid-matrix of waveform sub-segments, N=IO, according to some embodiments of the invention.
Figure 16:
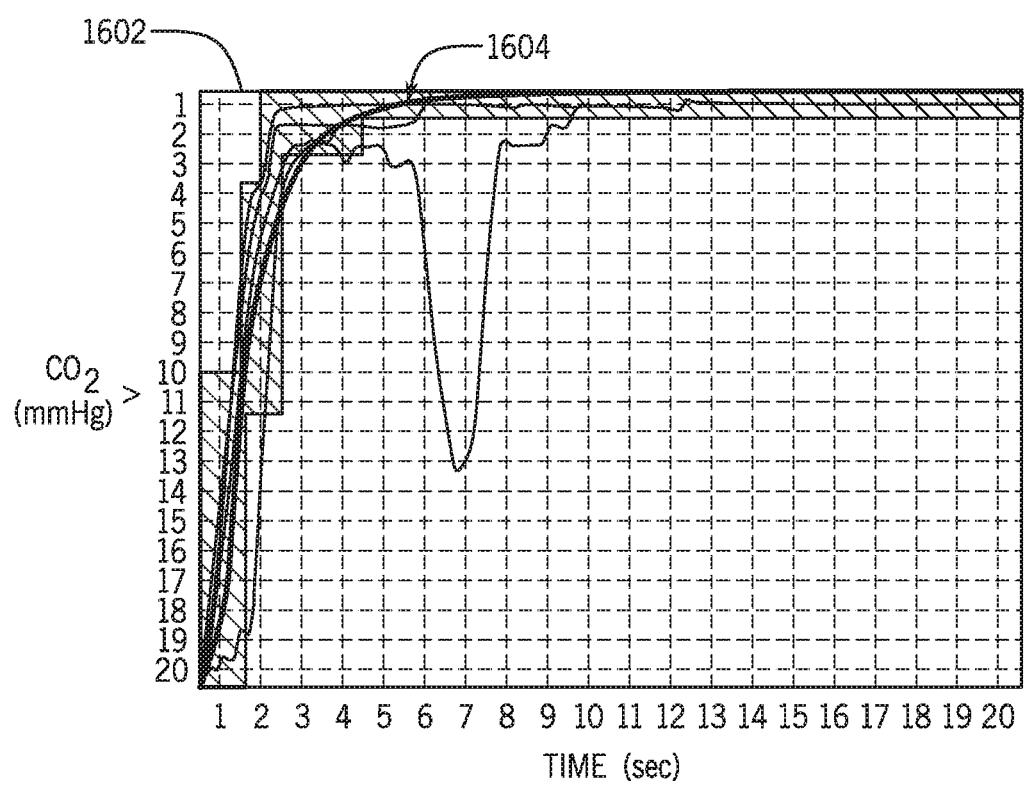
FIG. 16 shows the optimal pathway with an overlay of the original waveform sub-segments and the best-fit, according to some embodiments of the invention.

Examples for steps 640-644 of flow chart 600 of FIG. 6B can be found in FIGS. 15 and 16.

FIG. 15 shows the summed grid-matrix of waveform sub-segments (upstroke part of the whole breathing waveform) with N=10 (wherein N is the number of waveform sub-segments). The Shades indicate the number of gridded-waves that passed through each square in the matrix. The stars represent the optimal pathway.

FIG. 16 shows the optimal pathway with an overlay of the original (normalized) waveform sub-segments 1602 and the best-fit 1604 (from a set of preselected functions of waveforms, function bank/database). Returning to flow chart 600 of FIG. 6B, the next step after step 644, is step 650, which includes scale back and combining the representative normalized waveform sub-segments (if applicable), as disclosed hereinabove.

According to some embodiments, the methods disclosed herein allow memorizing a large history and or number of waveform data by just remembering the representative waveform characteristic parameters and using a driver to reconstruct the waveform on demand. This condensed manner of saving memory, may allow scrolling through representative waveforms over time, moving back to baselines or events, comparing with last "z" minutes or any other period of time or number of waveforms.

According to some embodiments, any of the methods disclosed herein may further provide a confidence index (graphical or value), which may be a measure of how dominant the representative waveform is. This confidence level may be based on how many artifacts were there and/or dispersion of the data building the representative waveform. According to some embodiments, any of the methods disclosed herein may further provide a measure of the dispersion (graphical or value) of one or more given important scale factor parameters for example, height, width or I to E (Inhalation to Exhalation) ratio.

In the description and claims of the application, each of the words "comprise" "include" and "have", and forms thereof, are not necessarily limited to members in a list with which the words may be associated.

The invention has been described using various detailed descriptions of embodiments thereof that are provided by way of example and are not intended to limit the scope of the invention. The described embodiments may comprise different features, not all of which are required in all embodiments of the invention. Some embodiments of the invention utilize only some of the features or possible combinations of the features. Variations of embodiments of the invention that are described and embodiments of the invention comprising different combinations of features noted in the described embodiments will occur to persons with skill in the art. It is intended that the scope of the invention be limited only by the claims and that the claims be interpreted to include all such variations and combinations.

What is claimed is:

1. A method, comprising:
obtaining a set of two or more $CO_2$ waveforms from a patient;
identifying a unique pattern in the two or more $CO_2$ waveforms, wherein the unique pattern comprises a recurring pattern that recurs over a predetermined number of consecutive waveforms of the two or more $CO_2$ waveforms, and wherein the recurring pattern is representative of a physiological condition;
removing the unique pattern from the two or more $CO_2$ waveforms;
determining one or more shape factors for each of the two or more $CO_2$ waveforms from which the unique pattern has been removed;
computing a representative set of shape factors based on the one or more shape factors for each of the two or more $CO_2$ waveforms from which the unique pattern has been removed;
constructing a representative $CO_2$ waveform based at least in part on the representative set of shape factors, such that the representative $CO_2$ waveform is representative of the shape of the two or more $CO_2$ waveforms from which the unique pattern has been removed;
superimposing the removed unique pattern on the representative $CO_2$ waveform to obtain a final representative $CO_2$ waveform; and
displaying the final representative $CO_2$ waveform overlaid on a background waveform on a display.

2. The method of claim 1, comprising determining one or more scale factors for each of the two or more $CO_2$ waveforms from which the unique pattern has been removed and computing a representative set of scale factors based on the one or more scale factors for each of the two or more $CO_2$ waveforms from which the unique pattern has been removed, and constructing the representative $CO_2$ waveform based at least in part on the representative sets of shape factors and scale factors, such that the representative $CO_2$ waveform is representative of both the shape and scale of the two or more $CO_2$ waveforms from which the unique pattern has been removed.

3. The method of claim 1, wherein the background waveform is a baseline $CO_2$ waveform associated with the patient.

4. The method of claim 3, wherein the baseline $CO_2$ waveform comprises a $CO_2$ waveform obtained at a certain time or condition, or a representative $CO_2$ waveform of $CO_2$ waveforms obtained at the certain time or condition.

5. The method of claim 1, wherein the background waveform comprises a textbook waveform.

6. The method of claim 1, wherein the background waveform comprises an area depicting a normal range of $CO_2$ waveforms associated with the patient.

7. The method of claim 1, wherein the background waveform comprises one or more preceding representative $CO_2$ waveforms to show a trend over time.

8. The method of claim 7, wherein the one or more preceding representative $CO_2$ waveforms are displayed starting from a same predetermined point of a breath cycle of the patient.

9. The method of claim 7, wherein the one or more preceding representative $CO_2$ waveforms are displayed in succession, such that one preceding representative $CO_2$ waveform starts at a point where another preceding representative $CO_2$ waveform ends.

10. The method of claim 1, comprising providing a confidence index indicative of a reliability of the representative $CO_2$ waveform, wherein the confidence index is based at least in part on dispersion of data used to construct the representative $CO_2$ waveform.

11. The method of claim 1, comprising removing $CO_2$ waveforms having artifacts from the set of two or more $CO_2$ waveforms, wherein the artifacts are identified based on predefined patterns, appearance, shape, position, or a combination thereof.

12. The method of claim 11, comprising providing a confidence index indicative of a reliability of the representative $CO_2$ waveform, wherein the confidence index is based at least in part on a number of artifacts removed, dispersion of data used to construct the representative $CO_2$ waveform, or a combination thereof.

13. An apparatus comprising a control logic configured to determine a representative $CO_2$ waveform associated with a patient, wherein the representative $CO_2$ waveform comprises a single waveform computed based on an integration of a representative set of shape and scale factors, wherein the representative set of shape factors is determined based on one or more shape factors, wherein the representative set of scale factors is determined based on one or more scale factors, wherein each of the representative set of shape factors and the representative set of scale factors represent two or more measured $CO_2$ waveforms from which a unique pattern has been identified and removed, wherein the unique pattern is a recurring pattern that recurs over a predetermined number of consecutive waveforms of the two or more $CO_2$ waveforms, wherein the recurring pattern is representative of a physiological condition, and wherein the apparatus further comprises a display unit configured to display the representative $CO_2$ waveform and a confidence index indicative of a reliability of the representative $CO_2$ waveform.

14. The apparatus of claim 13, wherein the confidence index is based at least in part on a number of artifacts removed from the two or more measured $CO_2$ waveforms prior to the removal of the unique pattern, dispersion of data used to construct the representative $CO_2$ waveform, or a combination thereof.

15. The apparatus of claim 13, wherein the display unit is further configured to display the representative $CO_2$ waveform overlaid on a background waveform.

16. The apparatus of claim 15, wherein the background waveform comprises one or more preceding representative $CO_2$ waveforms to show a trend over time.

17. The apparatus of claim 16, wherein the representative $CO_2$ waveform and the one or more preceding representative $CO_2$ waveforms are displayed starting from a same predetermined point in a breath cycle of the patient.

18. The apparatus of claim 16, wherein the one or more preceding representative $CO_2$ waveforms are displayed in succession, such that one preceding representative $CO_2$ waveform starts at a point where another preceding representative $CO_2$ waveform ends.

19. An apparatus comprising a control logic configured to determine a representative $CO_2$ waveform associated with a patient and to update the representative $CO_2$ waveform at an update rate, wherein the representative $CO_2$ waveform comprises a single waveform computed based on an integration of a representative set of shape and scale factors, wherein said representative set of shape factors is determined based on one or more shape factors, wherein said representative set of scale factors is determined based on one or more scale factors, wherein each of the representative set of shape factors and the representative set of scale factors represent two or more measured $CO_2$ waveforms from which a unique pattern has been identified and removed, wherein the unique pattern is a recurring pattern that recurs over a predetermined number of consecutive waveforms of the two or more $CO_2$ waveforms, and wherein the recurring pattern is representative of a physiological condition.

20. The apparatus of claim 19, wherein the update rate is defined by a function of parameters or conditions comprising respiration rate, age of the patient, a disease or disorder of the patient, or a combination thereof, and wherein the update rate is dynamic.

* * * * *